United States Patent
Neumann

(10) Patent No.: US 12,417,833 B2
(45) Date of Patent: Sep. 16, 2025

(54) SYSTEMS AND METHODS FOR GENERATING A CANCER ALLEVIATION NOURISHMENT PLAN

(71) Applicant: KPN INNOVATIONS, LLC., Lakewood, CO (US)

(72) Inventor: Kenneth Neumann, Lakewood, CO (US)

(73) Assignee: KPN INNOVATIONS, LLC., Lakewood, CO (US)

( * ) Notice: Subject to any disclaimer, the term of this patent is extended or adjusted under 35 U.S.C. 154(b) by 0 days.

(21) Appl. No.: 17/136,084

(22) Filed: Dec. 29, 2020

(65) Prior Publication Data

US 2022/0208337 A1  Jun. 30, 2022

(51) Int. Cl.
*G16H 20/60* (2018.01)
*A61B 5/00* (2006.01)
(Continued)

(52) U.S. Cl.
CPC ............ *G16H 20/60* (2018.01); *A61B 5/4842* (2013.01); *A61B 5/7267* (2013.01); *G16H 10/40* (2018.01);
(Continued)

(58) Field of Classification Search
CPC ........ G16H 20/60; G16H 50/30; G16H 50/70; G16H 10/60; G16H 10/40; G16H 50/20; G16H 10/20; A61B 5/7267; A61B 5/4842
See application file for complete search history.

(56) References Cited

U.S. PATENT DOCUMENTS

| 7,054,758 B2 | 5/2006 | Gill-Garrison |
| 8,731,970 B2 * | 5/2014 | Hermann ............... G16H 20/40 705/3 |
| 2008/0193482 A1 * | 8/2008 | Woodward ........... A61K 38/191 424/227.1 |

(Continued)

FOREIGN PATENT DOCUMENTS

WO    2016055829    4/2016

OTHER PUBLICATIONS

Veselkov, K., Gonzalez, G., Aljifri, S. et al. HyperFoods: Machine intelligent mapping of cancer-beating molecules in foods. Sci Rep 9, 9237 (2019). https://doi.org/10.1038/s41598-019-45349-y (Year: 2019).*

(Continued)

*Primary Examiner* — Eliza A Lam
(74) *Attorney, Agent, or Firm* — Caldwell Intellectual Property Law

(57) ABSTRACT

A system for generating a cancer alleviation nourishment plan includes a computing device configured to receive at least a cancer biomarker, retrieve a cancer profile, identify, using the cancer profile, a plurality of nutrition elements, including assigning the cancer profile to a cancer category, wherein the cancer category summarizes the current malignancy state of the user, calculating, according to the cancer category, a plurality of nutrient amounts, wherein calculating the plurality of nutrient amounts includes determining an effect on the cancer profile and calculating the plurality of nutrient amounts as a function of the effect, wherein the plurality of nutrient amounts is intended to result in cancer prevention, identifying, as a function of the plurality of nutrient amounts, the plurality of nutrition elements, wherein the plurality of nutrition elements contain the plurality of nutrient amounts, and generate, using the plurality of nutrition elements, the cancer prevention nourishment plan.

18 Claims, 8 Drawing Sheets

(51) Int. Cl.
    *G16H 10/40*        (2018.01)
    *G16H 10/60*        (2018.01)
    *G16H 50/20*        (2018.01)
    *G16H 50/30*        (2018.01)
    *G16H 50/70*        (2018.01)

(52) U.S. Cl.
    CPC ............ *G16H 10/60* (2018.01); *G16H 50/20* (2018.01); *G16H 50/30* (2018.01); *G16H 50/70* (2018.01)

(56) References Cited

U.S. PATENT DOCUMENTS

| | | | |
|---|---|---|---|
| 2008/0275912 A1 | 11/2008 | Roberts | |
| 2010/0042438 A1* | 2/2010 | Moore | G16B 20/00 705/3 |
| 2011/0093295 A1 | 4/2011 | Mankad | |
| 2013/0261183 A1 | 10/2013 | Bhagat | |
| 2013/0338020 A1* | 12/2013 | Ross | C12Q 1/6886 506/9 |
| 2017/0068777 A1 | 3/2017 | Parnell | |
| 2018/0190375 A1* | 7/2018 | Chapela | A61B 5/486 |
| 2020/0164209 A1* | 5/2020 | Hogg | A61N 1/36014 |
| 2020/0243202 A1 | 7/2020 | Subra | |

OTHER PUBLICATIONS

Shiao SPK, Grayson J, Lie A, Yu CH. Personalized Nutrition-Genes, Diet, and Related Interactive Parameters as Predictors of Cancer in Multiethnic Colorectal Cancer Families. Nutrients. Jun. 20, 2018;10(6):795. doi: 10.3390/nu10060795. PMID: 29925788; PMCID: PMC6024706. (Year: 2018).* https://www.researchgate.net/publication/221855801; Title: Nutrigenomics: Implications for Breast and Colon Cancer Prevention; By: Riscuta et al.; Date: 2012.

https://doi.org/10.1111/j.1745-7254.2007.00678.x; Title: Biomarkers for diet and cancer prevention research: potentials and challenges; By: Davis; Date: 2007.

https://doi.org/10.1016/B978-0-12-816151-7.00019-3; Title: Harnessing personalized nutrigenomics for cancer prevention and treatment through diet-gene interaction; By: Rahman; Date: 2020.

https://doi.org/10.3390/nu10060795; Title: Personalized Nutrition—Genes, Diet, and Related Interactive Parameters as Predictors of Cancer in Multiethnic Colorectal Cancer Families; By Pamela K. Shiao; Date: Jun. 20, 2018.

https://doi.org/10.2217/pme.14.2; Title: Nutrigenetics and personalized nutrition: are we ready for DNA-based dietary advice?; By: Grimaldi; Date: 2014.

* cited by examiner

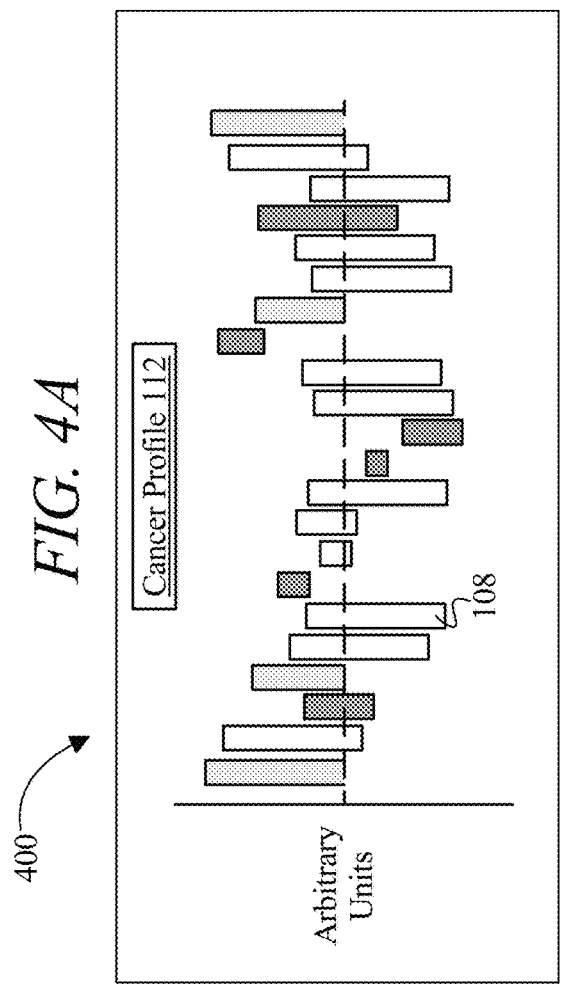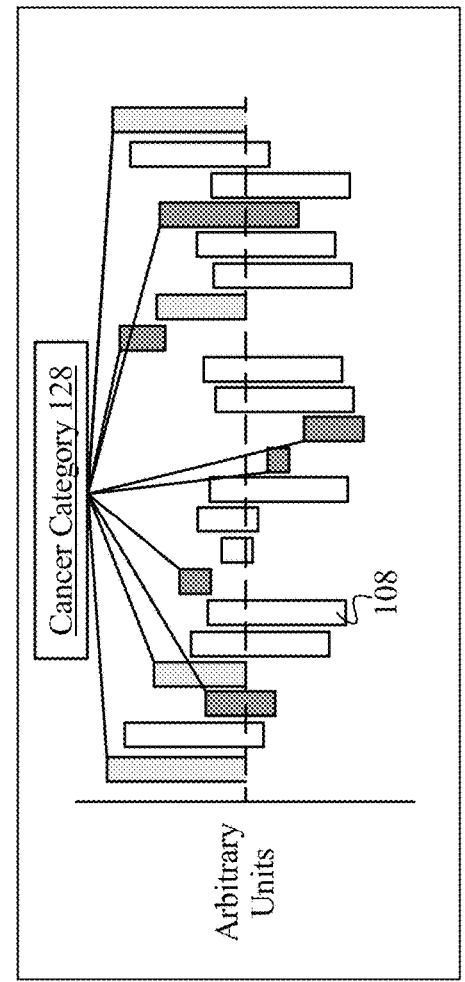

SYSTEMS AND METHODS FOR GENERATING A CANCER ALLEVIATION NOURISHMENT PLAN

FIELD OF THE INVENTION

The present invention generally relates to the field of nutrition planning for cancer prevention. In particular, the present invention is directed to systems and methods for generating a cancer alleviation nourishment plan.

BACKGROUND

It has been estimated that 30-40 percent of all cancers may be prevented by lifestyle measures. Obesity, nutrient sparse foods such as concentrated sugars and refined flour products that contribute to impaired glucose metabolism, low fiber intake, consumption of red meat, and imbalance of omega fatty acids may all contribute to excess cancer risk. Intake of particular ingredients, especially lignan fractions of plants, and abundant portions of fruits and vegetables may have an effect on cancer risk. Substantial experimental evidence indicates the potential importance of dietary and nutritional factors in cancer prevention but identifying relationships between diet and cancer in observational epidemiological and intervention trials has proved challenging.

SUMMARY OF THE DISCLOSURE

In an aspect, a system for generating a cancer alleviation nourishment plan including a computing device configured to receive at least a cancer biomarker relating to a user, retrieve a cancer profile related to the user, assign the cancer profile to a cancer category, wherein the cancer category includes a determination of a current malignancy state of the user, identify, using the cancer profile, a plurality of nutrition elements for the user, wherein identifying includes calculating, according to the cancer category, a plurality of nutrient amounts, wherein calculating the plurality of nutrient amounts includes determining a respective effect of each nutrient amount of the plurality of nutrient amounts on the cancer profile, and calculating each of the nutrient amounts of the plurality of nutrient amounts as a function of the respective effect of each the plurality of nutrient amounts, wherein the plurality of nutrient amounts comprises a plurality of amounts intended to result in cancer alleviation corresponding to the cancer category, identifying, as a function of the plurality of nutrient amounts, the plurality of nutrition elements for cancer alleviation, and generate, using the plurality of nutrition elements, a cancer alleviation nourishment plan.

In another aspect, a method for generating a cancer alleviation nourishment plan including receiving, by a computing device, at least a cancer biomarker relating to a user, retrieving, by the computing device, a cancer profile related to the user, assigning, by the computing device, the cancer profile to a cancer category, wherein the cancer category includes a determination of a current malignancy state of the user, identifying, by the computing device, using the cancer profile, a plurality of nutrition elements for the user, wherein identifying includes calculating, according to the cancer category, a plurality of nutrient amounts, wherein calculating the plurality of nutrient amounts includes determining a respective effect of each nutrient amount of the plurality of nutrient amounts on the cancer profile, and calculating each of the nutrient amounts of the plurality of nutrient amounts as a function of the respective effect of each the plurality of nutrient amounts, wherein the plurality of nutrient amounts comprises a plurality of amounts intended to result in cancer alleviation corresponding to the cancer category, identifying, as a function of the plurality of nutrient amounts, the plurality of nutrition elements for cancer alleviation, and generating, by the computing device, using the plurality of nutrition elements, a cancer alleviation nourishment plan.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIGS. 4A and 4B are a diagrammatic representation of a cancer profile;

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for generating a cancer alleviation nourishment plan. In an embodiment, system includes a computing device configured to receive cancer biomarkers of a user. Cancer biomarkers may include experimental testing results, such as genetic sequencing data, blood panel, lipid panel, etc. Computing device is configured to retrieve a cancer profile corresponding to the user. Computing device may generate cancer profile, by using a machine-learning algorithm to model cancer biomarkers to malignancies parameters. Computing device may enumerate malignancies parameters in the cancer profile, and classify the user to a cancer category, for instance using a machine-learning classifier. Computing device is configured to determine the effect of nutrients on the user's cancer profile and calculate nutrient amounts according to the effect that may prevent, or otherwise address, cancer biomarkers identified of the user. Computing device may identify nutrition elements, such as an individual ingredients, and calculate a nourishment plan, including combinations of the ingredients to achieve the calculate nutrition amounts. Computing device may accept user preferences regarding nutrition elements and generate a cancer prevention nourishment plan, wherein items are curated according to the user's unique cancer profile and nutrition element preferences. Participation and adherence to nourishment plan may be provided a nourishment score for tracking cancer prevention.

Figure 1:
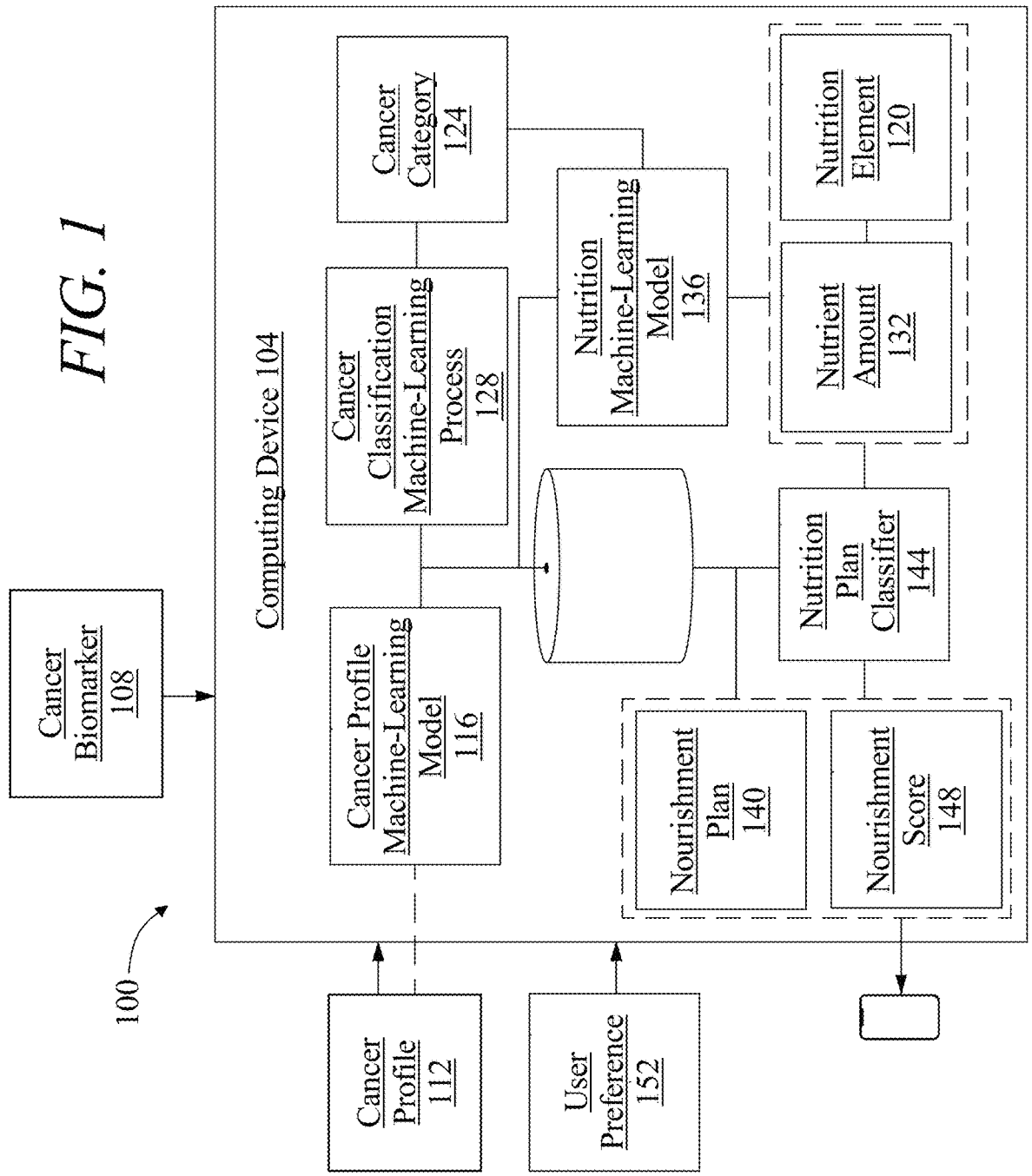
FIG. 1 is a block diagram illustrating a system for generating a cancer alleviation nourishment plan.

Referring now to FIG. 1, an exemplary embodiment of a system 100 for generating a cancer alleviation nourishment plan is illustrated. System includes a computing device 104. Computing device 104 may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Computing device 104 may include a single computing device operating independently, or may include two or more computing device operating in concert, in parallel, sequentially or the like; two or more computing devices may be included together in a single computing device or in two or more computing devices. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Computing device 104 may include but is not limited to, for example, a computing device or cluster of computing devices in a first location and a second computing device or cluster of computing devices in a second location. Computing device 104 may include one or more computing devices dedicated to data storage, security, distribution of traffic for load balancing, and the like. Computing device 104 may distribute one or more computing tasks as described below across a plurality of computing devices of computing device, which may operate in parallel, in series, redundantly, or in any other manner used for distribution of tasks or memory between computing devices. Computing device 104 may be implemented using a "shared nothing" architecture in which data is cached at the worker, in an embodiment, this may enable scalability of system 100 and/or computing device.

With continued reference to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Continuing in reference to FIG. 1, computing device is configured to receive at least a cancer biomarker related to a user. A "cancer biomarker," as used in this disclosure, is a biological and/or chemical substance or process that is indicative of the presence of cancer in the body. Cancer biomarker 108 may include biological molecules existing within a normal cell, a cancerous cell, secreted by a tumor, and/or a specific response of the body to the presence of cancer. Receiving at least the cancer biomarker 108 may include receiving a result of one or more tests relating the user. Cancer biomarker 108 may include test results of screening and/or early detection of cancer, diagnostic procedures, prognostic indicators from other diagnoses, from predictors identified in a medical history, and information relating to biomolecules associated with malignancy such as: ATM, BRCA 1, BRCA 2, BARD1, CDH1, CHEK2, EGFR, EPCAM, erB2, FANCC, KRAS, MLH1, MRE11, MSH2, MSH6, MUTYH, NBN, NF1, p52, PALB2, PMS2, PTEN, RAD50, STK11, TP53 (p53), XRCC, abnormal DNA methylation patterns, gene expression patterns, gene regulation, the presence of particular miRNAs and other non-coding RNAs (ncRNAs), CA-125, CBC, blood protein testing, tumor marker testing, circulating tumor cell tests, flow cytometry, thyroglobulin, and the like. A person skilled in the art having the benefit of the entirety of this disclosure will be aware of various additional tests and/or biomarkers that may be used and or received to receive cancer biomarker.

Continuing in reference to FIG. 1, such a test may include results enumerating the identification of mutations in DNA sequences. Test results may indicate the presents of single nucleotide polymorphisms (SNPs) in genetic sequences. Test results may indicate epigenetic factors indicative of cancer. Cancer biomarker 108 may include hematological analysis including results from T-cell activation assays, abnormal nucleation of white blood cells, white blood cell counts, concentrations, recruitment and localization, and the like. Cancer biomarker 108 may be received as a function of a user indicating a prior diagnosis, XRT treatment, chemotherapy regimen, etc., such as "current medications," wherein one is a cancer treatment. Cancer biomarker 108 may include any cancer-related symptoms, side effects, and co-morbidities associated with and relating to cancer diagnosis, treatment and/or remission, such as metallic taste in mouth from chemotherapy, decreased bone density after chemotherapy, skin burning/rash/scarring from radiation treatment, hair loss, nail bed damage, onset of sclerosis, foggy memory, etc. Cancer biomarker 108 may be received and/or identified from a biological extraction of a user, which may include analysis of a physical sample of a user such as blood, DNA, saliva, stool, and the like, without limitation and as described in U.S. Nonprovisional application Ser. No. 16/886,647, filed May 28, 2020, and entitled, "METHODS AND SYSTEMS FOR DETERMINING A PLURALITY OF BIOLOGICAL OUTCOMES USING A PLURALITY OF DIMENSIONS OF BIOLOGICAL EXTRACTION USER DATA AND ARTIFICIAL INTELLIGENCE," the entirety of which is incorporated herein by reference.

Continuing in reference to FIG. 1, cancer biomarker 108 may be organized into training data sets. "Training data," as used herein, is data containing correlations that a machine learning process, algorithm, and/or method may use to model relationships between two or more categories of data elements. For instance, and without limitation, training data may include a plurality of data entries, each entry representing a set of data elements that were recorded, received, and/or generated together; data elements may be correlated by shared existence in a given data entry, by proximity in a given data entry, or the like. Multiple data entries in training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data according to various correlations; correlations may indicate causative and/or predictive links between categories of data elements, which may be modeled as relationships such as mathematical relationships by machine learning processes as described in further detail below.

Continuing in reference to FIG. 1, cancer biomarker 108 may be used to generate training data for a machine-learning process. A "machine learning process," as used in this disclosure, is a process that automatedly uses a body of data known as "training data" and/or a "training set" to generate an algorithm (such as a collection of one or more functions, equations, and the like) that will be performed by a machine-learning module to produce outputs given data provided as inputs; this is in contrast to a non-machine learning software programing where the commands to be executed are determined in advance by a subject and written in a programming language, as described in further detail below.

Continuing in reference to FIG. 1, cancer biomarker 108 may be organized into training data sets and stored and/or retrieved by computing device 104, without limitation, as a relational database, a key-value retrieval database such as a NOSQL database, or any other format or structure for use as a database that a person skilled in the art would recognize as suitable upon review of the entirety of this disclosure. Cancer biomarker 108 training data may alternatively or additionally be implemented using a distributed data storage protocol and/or data structure, such as a distributed hash table and the like. Cancer biomarker 108 training data may include a plurality of data entries and/or records, as described above. Data entries may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries of cancer biomarkers may be stored, retrieved, organized, and/or reflect data and/or records as used herein, as well as categories and/or populations of data consistent with this disclosure.

Continuing in reference to FIG. 1, computing device is configured to retrieve a cancer profile related to the user. A "cancer profile," as used in this disclosure, is a profile that summarizes a user's current state with regard to cancer. Cancer profile 112 may include at least a malignancy parameter, A "malignancy parameter," as used in this disclosure, is a quantitative metric that encapsulates a current state of cancer in the user according to the presence of at least a cancer biomarker 112. A current state of cancer may include a current propensity for developing a malignancy. A current state of cancer may include "no malignancy". In individuals harboring no malignancy, a current state of cancer may include a tissue, organ, cancer type, etc., with which the user most closely resembles, or has a likelihood of developing in the future. Malignancy parameter may be malignancy-specific, for instance and without limitation, a numerical value for each of 100+ cancer types, where the numerical value is a likelihood that a cancer biomarker 108 relates to a solid tumor, a metastasis, a particular cancer, etc. Cancer profile 112 may include any medical, physiological, biological, chemical, and/or physical determination about the current state of a user's propensity for cancer, including their "current likelihood for cancer", and projected, future likelihood for cancer. Cancer profile 112 may include qualitative and/or quantitative (malignancy parameter) summarization of the presence of malignant tissue, metastasis, solid tumors, circulating tumor cells, biomarkers indicative of cancer, current risk of cancer, future risk of cancer, lifetime risk of cancer, biomarkers classified to cancer types, and the like. Cancer profile 112 may include qualitative determinations, such as binary "yes"/"no" determinations for cancer types, "normal"/"abnormal" determinations about the presence of and/or concentration of cancer biomarkers 108, for instance as compared to a normalized threshold value of a biomarker among healthy adults. Cancer profile 112 may include a plurality of malignancy parameters, wherein malignancy parameters are quantitative determinations such as a "cancer score", which may include any metric, parameter, or numerical value that communicates a cancer state. Cancer profile 112 may include malignancy parameters that are mathematical representations of the current state of cancer, such as a function describing the cancer risk as a function of time. Malignancy parameters may be cancer-specific, tissue-specific, biological pathway-specific, etc. Cancer profile 112 may include instantaneous cancer risk, such as weekly, monthly, annual, etc., cancer risk, classified by cancer type, according to medical history, biological extraction result, and the like.

Continuing in reference to FIG. 1, retrieving cancer profile 112 may include receiving cancer profile training data. "Cancer profile training data" may include cancer biomarkers 112 organized into training data sets, as described above, including results from biological extraction samples, health state questionnaires regarding symptomology, medical histories, physician assessments, lab work, and the like. Cancer profile training data may originate from the subject, for instance via a questionnaire and a user interface with computing device 104, for user to provide medical history data. Receiving cancer profile training data may include receiving whole genome sequencing, gene expression patterns, and the like, for instance as provided by a genomic sequencing entity, hospital, database, the Internet, etc. Cancer profile training data may include raw data values recorded and transmitted to computing device 104 via a wearable device such as a pedometer, gyrometer, accelerometer, motion tracking device, bioimpedance device, ECG/EKG/EEG monitor, physiological sensors, blood pressure monitor, blood sugar and volatile organic compound (VOC) monitor, and the like. Cancer profile training data may originate from an individual other than user, including for instance a physician, lab technician, nurse, caretaker, psychologist, therapist, and the like. Cancer profile training data may be input into computing device 104 for instance via a health state questionnaire for onboarding of user symptomology, via a graphical user interface. It is important to note that training data for machine-learning processes, algorithms, and/or models used in system 100 herein may originate from any source described for cancer profile training data.

Continuing in reference to FIG. 1, a "graphical user interface," as used in this disclosure, is any form of a user interface that allows a user to interface with an electronic device through graphical icons, audio indicators, text-based interface, typed command labels, text navigation, and the like, wherein the interface is configured to provide information to the user and accept input from the user. Graphical user interface may accept input, wherein input may include an interaction (such as a questionnaire) with a user device. A user device, as described in further detail below, may include computing device 104, a "smartphone," cellular mobile phone, desktop computer, laptop, tablet computer, internet-of-things (JOT) device, wearable device, among other devices. User device may include any device that is capable for communicating with computing device 104, database, or able to receive data, retrieve data, store data, and/or transmit data, for instance via a data network technology such as 3G, 4G/LTE, 5G, Wi-Fi (IEEE 802.11 family standards), and the like. User device may include devices that communicate using other mobile communication technologies, or any combination thereof, for short-range wireless communication (for instance, using Bluetooth and/or Bluetooth LE standards, AirDrop, Wi-Fi, NFC, etc.), and the like.

Continuing in reference to FIG. 1, retrieving cancer profile 112 may include training a cancer profile machine-learning model with cancer profile training data that includes a plurality of data entries wherein each entry correlates cancer biomarkers 112 to a plurality of malignancy parameters. Cancer profile machine-learning model 116 may include any machine-learning algorithm (such as K-nearest neighbors algorithm, a lazy naïve Bayes algorithm, etc.), machine-learning process (such as supervised machine-learning, unsupervised machine-learning), or method (such as neural nets, deep learning, etc.). Cancer profile machine-learning model 116 may be trained to derive the algorithm, function, series of equations, or any mathematical operation, relationship, or heuristic, that can automatedly accept an input (cancer biomarker(s) 108) and correlate, classify, or otherwise calculate an output (malignancy parameter(s)). Cancer profile machine-learning model 116 may include individual functions, derived for unique relationships observed from the training data for each cancer biomarker 108. In non-limiting illustrative examples, the expression levels of a variety of oncogenic genes in human tissues, as identified above, may be retrieved from a database, such as a repository of peer-reviewed research (e.g. National Center for Biotechnology Information is part of the United States National Library of Medicine), and the cancer profile machine-learning model 116 derived algorithm may observe an average and statistical evaluation (mean±S.D.) may be calculated from the data, across which the user's expression level is compared. In such an example, cancer profile machine-learning model 116 may derive an algorithm according to the data which may also include a scoring function that includes a relationship for how to arrive at a malignancy parameter numerical value score according to the user's level of gene expression (e.g. number of mRNA transcripts per tissue) as it relates to the average and statistical evaluation in normal tissue expression.

Continuing in reference to FIG. 1, cancer biomarker 108 may be correlated to a plurality of malignancy parameters without the use of machine-learning process(es). For instance and without limitation, computing device 104 may use a web browser and the Internet to identify a plurality of threshold values of gene expression that relate to cancer biomarkers 108 in "healthy adults", wherein gene expression values that deviate from such a threshold may indicate malignancy, and the magnitude of deviation relates to the magnitude of numerical value for malignancy parameter.

Continuing in reference to FIG. 1, retrieving the cancer profile 112 may include generating the cancer profile 112 using the cancer profile machine-learning model 116 and at least the cancer biomarker 108. Persons skilled in the art may appreciate that cancer profile 112 may become increasingly more complete, and more robust, with increasing numbers of malignancy parameters, describing larger sets of cancer biomarkers 108 in the user. Malignancy parameter may be generated for each gene (or set of genes) described above; each white blood cell type (or set of white blood cell type); among other factors. Cancer profile machine-learning model 116 may derive a unique algorithm for developing individual malignancy parameters from the plurality of cancer biomarkers 108. Cancer profile machine-learning model 116 may derive functions, systems of equations, matrices, etc., that describe and/or incorporate relationships between sets of cancer biomarkers 108 (training data), for instance combining the expression level of two or more genes, multiplied by scalar coefficients according to the presence of SNPs (single nucleotide polymorphisms) or mutations present in the genes, dividing by the ratio of phosphorylated-unphosphorylated states, ubiquitinated states, etc. In the full spectrum of cell signaling, maintaining cellular homeostasis, cell division, protein degradation, among other biological phenomenon that may contribute to the development of cancers, cancer profile machine-learning model 116 may derive increasingly complicated algorithms for combining cancer biomarkers 108 into malignancy parameters summarized in cancer profile 112.

Continuing in reference to FIG. 1, computing device 104 is configured to identify, using the cancer profile 112, a plurality of nutrition elements for the user. A "nutrition element," as used in this disclosure, is any item that includes a nutrient intended to be used and/or consumed by user for cancer alleviation. A "nutrient," as used in this disclosure," is any biologically active compound whose consumption is intended for the treatment and/or prevention of cancer. Nutrition element 120 may include alimentary elements, such as meals (e.g. chicken parmesan with Greek salad and iced tea), food items (e.g. French fries), grocery items (e.g. broccoli), health supplements (e.g. whey protein), beverages (e.g. orange juice), and the like. Nutrition element 120 may be "personalized" in that nutrition elements are curated in a guided manner according to cancer profile 112, gene expression patterns, cancer biomarkers 108, SNPs, the Warburg Effect, a cancer category (liver, lung, pancreatic, brain, breast, blood, carcinoma, melanoma, Stage I, Stage II, etc.), treatment type (T-Car therapy, hormone treatment, surgery, taxanes, cisplatin, etc.), and the like. Nutrition element 120 may include supplementary use of oral digestive enzymes and probiotics which may also have merit as anticancer measures. Nutrition elements 120 in a cancer prevention diet may include selenium, folic acid, vitamin B-12, vitamin D, chlorophyll, and antioxidants such as the carotenoids (α-carotene, β-carotene, lycopene, lutein, cryptoxanthin). Nutrient elements 120 may contain biological active compounds that are not typically considered vitamins and/or minerals, nor are they intended to provide appreciable amounts of calories, such as phytonutrients and antioxidants; for instance allium and bioactive ingredients present in cruciferous vegetables such as broccoli sprouts, which are known sources of antioxidants such as sulforaphane, which may have therapeutic effects on cancerous cells. Nutrition elements 120 may include a specific dietary category, such as a "ketogenic diet", "low glycemic index diet", "Paleo diet", and so on.

Continuing in reference to FIG. 1, identifying the plurality of nutrition elements 120 includes assigning the cancer profile 112 to a cancer category, wherein the cancer category is a determination about a current malignancy state of the user. A "cancer category," as used in this disclosure, is a designation of a cancer type. Cancer category 124 may include tissue or organ type, such as "liver cancer", "lung cancer", "skin cancer", etc. Cancer category 124 may include a designation regarding a cancer type that may not involve a particular tissue such as "sarcoma", "carcinoma", "lymphoma", etc. Cancer category 124 may include pathological, histological, and/or clinical classification identifiers such as "Stage I-IV" classification system, presence of metastasis, spread to lymph nodes, etc. Cancer category 124 may include identifiers associated with metastasis, remission rates, and survivability. Cancer category 124 may include a predictive cancer classification, where a user does not currently harbor a particular malignancy but may include data that indicates a cancer category 124 with which they may be most closely categorized to. For instance, a family history of breast cancer due to a combination of hereditary genetic elements (as summarized in cancer profile 112) may classify an individual in "breast cancer" cancer category 124, despite not currently having breast cancer. Cancer profile 112 may have associated with it an identifier, such as a label, that corresponds to a cancer category 124.

Continuing in reference to FIG. 1, assigning the cancer profile to a cancer category may include classifying the cancer profile 112 to a cancer category 124 using a cancer classification machine-learning process. Classification using cancer classification machine-learning process 128 may include identifying which set of categories (cancer category 124) an observation belongs (cancer profile 112). Classification may include clustering based on pattern recognition, wherein the presence of cancer biomarkers 108, such as genetic indicators, symptoms, and the like, identified in cancer profile 112 relate to a particular cancer category 124. Such classification methods may include binary classification, where the cancer profile 112 is simply matched to each existing cancer category 124 and sorted into a category based on a "yes"/"no" match. Classification done in such a manner may include weighting, scoring, or otherwise assigning a numerical value to elements in cancer profile 112 as it relates to each cancer type and assign a user to a cancer category 124 for the cancer type that results in the highest score. Such a score may represent a "likelihood", probability, or other numerical data that relates to the classification into cancer category 124.

Continuing in reference to FIG. 1, cancer classification machine-learning process 128 may include any machine-learning process, method, and/or algorithm, as described in further detail below. Cancer classification machine-learning process 128 may generate a "classifier" using training data. A classifier may include a machine-learning model, such as a mathematical model, neural net, or program generated by a machine learning algorithm known as a "classification algorithm," as described in further detail below. Such a classifier may sort inputs (such as the data in the cancer profile 112) into categories or bins of data (such as classifying the data into a cancer category), outputting the bins of data and/or labels associated therewith. Training data used for such a classifier may include a set of cancer profile 112 training data as it relates to classes of cancer types, organ/tissue, types, etc. For instance, training data may include ranges of biomarkers as they relate to various cancer types, severity of cancer (Stage I-IV), and the like. Using datasets of this data as training data to train a classifier to derive relationships present in the data that may result in a machine-learning model that automatedly classifies a user to a cancer category as a function of the data present in their cancer profile 112. A classifier may be configured to output at least a datum that labels or otherwise identifies a set of data that are clustered together, found to be close under a distance metric as described below, or the like. Machine-learning module, as described in further detail below. may generate a classifier using a classification algorithm, defined as a process whereby a computing device and/or any module and/or component operating thereon derives a classifier from training data. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, a cancer profile 112 training data classifier may classify elements of training data to elements that characterizes a sub-population, such as a subset of cancer biomarker 108 (such as gene expression patterns as it relates to a variety of cancer types) and/or other analyzed items and/or phenomena for which a subset of training data may be selected.

Continuing in reference to FIG. 1, classifying the cancer profile 112 (input) to a cancer category 124 (output) may include assigning the cancer category 124 as a function of the cancer classification machine-learning process 128 and the cancer profile 112. Training data may include sets of malignancy parameters and/or cancer biomarkers 108, as described above. Such training data may be used to "learn" how to categorize a user's cancer profile 112 to cancer categories depending on trends in mutations, gene expression, SNPs, user symptomology, and the like. Training data for such a classifier may originate from user input, for instance via a health state questionnaire via a graphical user interface, may originate from a biological extraction test result such as genetic sequencing, blood panel, lipid panel. Training data may originate from a user's medical history, a wearable device, a family history of disease. Training data may similarly originate from any source, as described above, for cancer biomarker 108 and determining cancer profile 112.

Continuing in reference to FIG. 1, identifying the plurality of nutrition elements 120 includes calculating, according to the cancer category 124, a plurality of nutrient amounts, wherein calculating the plurality of nutrient amounts includes determining a respective effect of each nutrient amount of the plurality of nutrient amounts on the cancer profile 112. An "effect of a nutrient," as used in this disclosure, is a change, consequence, and/or result in at least a cancer biomarker 108, cancer profile 112, cancer category 124, and/or likelihood of cancer in a user due to consumption of an amount of a nutrient. An effect of a nutrient may be "no effect". Calculating an effect of a nutrient may include determining how a cancer biomarker 108 may change, such as an increase/decrease according to a particular amount of nutrient. For instance and without limitation, such a calculation may include determining the effect of chronic, sustained nutrient amounts in a diet for weeks, months, etc.

Continuing in reference to FIG. 1, determining the effect of the plurality of nutrient amounts on the cancer profile 112 may include retrieving a plurality of predicted effects of each nutrient amount of the plurality of nutrient amounts on the cancer profile 112 as a function of at least the cancer biomarker 108. A "predicted effect" of a nutrient or combination of nutrients as used in this disclosure, is a hypothesis about the outcome for a user after consuming a nutrient amount and/or amount of a combination of nutrients. Retrieving a plurality of predicted effects may include retrieving from a database, a research repository, or the like. Retrieving a plurality of effects may include, for instance, searching using the cancer profile 112, a web browser and the Internet, for a plurality of effects. In some embodiments retrieving a plurality of predicted effects may include calculating at least an effect, for instance by deriving a function from a machine-learning algorithm. A predicted effect of a plurality of nutrient amounts may include the effect on cancer category 124, cancer biomarker 108, malignancy parameter, likelihood of cancer, cancer risk, etc. from a particular nutrient amount, or combination of nutrient amounts.

Continuing in reference to FIG. 1, in non-limiting illustrative examples, determining an effect of a nutrient may include determining if a change in cancer category 124 may arise from adding and/or removing a nutrient from a user's diet, for instance changing a cancer category 124 from "skin cancer" to "gastric cancer" with increasing dietary vitamin E and vitamin K by introducing nutrition elements 120 a user is not accustomed (e.g. vegetable oils, soybeans, tree nuts, seeds, green leafy vegetables, etc.). Calculating an effect of a nutrient may include a mathematical operation, such as subtraction, addition, etc. Calculating an effect of a nutrient may include retrieving an empirical equation that describes relationships between a nutrient and cancer biomarker 108, test results, malignancy parameter, and the like. Calculating an effect of a nutrient may include deriving an algorithm, function, or the like, for instance using a machine-learning process and/or model. Calculating such an effect using machine-learning may include training data that includes a plurality of nutrients as it relates to effects on cancer categories 124, cancer biomarkers 108, etc.

Continuing in reference to FIG. 1, in non-limiting illustrative examples, oral vitamin C doses used past studies may produce peak plasma concentration of less than 200 micromolar ($\mu M$). In contrast, the same dose given intravenously, as used in the Pauling studies, would produce peak plasma concentrations of nearly 6 mM, more than 25 times higher. When given orally, vitamin C concentration in human plasma is tightly controlled by multiple mechanisms acting together: intestinal absorption, tissue accumulation, renal reabsorption, and excretion, and potentially even the rate of utilization. However, when ascorbate is administered intravenously or intraperitoneally the tight controls are bypassed, and pharmacologic millimolar plasma concentrations of vitamin C can easily be achieved. For example, phase I clinical studies revealed that ascorbate concentrations could safely reach 25-30 mM with intravenous infusion of 100 g of vitamin C, and thus super-high daily vitamin C dosages may also be supported. Plasma concentrations of up to 10 mM may be sustained for at least 4 hours which, based on preclinical studies, is sufficient to have an effect on cancer cells. Given the fact that cancer patients were only treated with vitamin C orally in the studies, the studies provide some evidence that high dose vitamin C efficacy may have efficacy in some patients. And, over the past decade, there have been an increased number of phase I/II clinical trials and case reports testing the safety and efficacy of high dose vitamin C as a treatment for various cancer patients, specifically as a conjunctive therapy in addressing chemotherapy-induced toxicity and co-morbidity. Thus, there is mounting evidence that specific cancer state to nutrient relationships may be found and observed in clinical data. And such data may reveal specific oral dosage to plasma concentration effects of each nutrient amount, wherein the nutrient amount may be found to be increased far above what would be normally considered to maintain a specific effect in a particular cancer patient.

Continuing in reference to FIG. 1, computing device 104 is configured for calculating each of the nutrient amounts of the plurality of nutrient amounts as a function of the respective effect of each the plurality of nutrient amounts, wherein the plurality of nutrient amounts comprises a plurality of amounts intended to result in cancer alleviation corresponding to the cancer category. Calculating nutrient amounts, may include determining an effect of a nutrient on the plurality of malignancy parameters in the cancer profile 112, wherein the effect of the nutrient is correlated to the malignancy parameter. A "nutrient amount," as used in this disclosure, is a numerical value(s) relating to the amount of a nutrient. Nutrient amount 132 may include mass amounts of a vitamin, mineral, macronutrient (carbohydrate, protein, fat), a numerical value of calories, mass amounts of phytonutrients, antioxidants, probiotics, nutraceuticals, bioactive ingredients, and the like. For example and without limitation, utilizing high doses of vitamin C may have an effect on malignancy parameters, which in-turn effect cancer profile 112. Cancer patients often present with severely low levels of vitamin C in the blood and feature scurvy-like symptoms, leading researchers to postulate that vitamin C may protect against cancer specifically by increasing collagen synthesis. However, this may have an effect on malignancy parameters, such as parameters describing metastasis and metastatic potential in patients. Researchers hypothesized that ascorbate could suppress cancer development by inhibiting hyaluronidase, which otherwise weakens the extracellular matrix and enables cancer to metastasize. Therefore, in such patients, vitamin C supplementation above what may be normally considered "recommended" may have an effect for increasing malignancy parameters associated with metastasis.

Continuing in reference to FIG. 1, computing device 104 may calculate nutrient amounts 132, for instance, by using a default amount, such as from a standard 2,000 calorie diet, and increasing and/or decreasing the amount according to a numerical scale associated with malignancy parameters in the cancer profile 112. Such a calculation may include a mathematical operation such as subtraction, addition, multiplication, etc.; alternatively or additionally, such a calculation may involve deriving a loss function, vector analysis, linear algebra, system of questions, etc., depending on the granularity of the process. Deriving such a process for the calculating may include machine-learning. Nutrient amounts 132 may include threshold values, or ranges or values, for instance and without limitation, between 80-120 mg vitamin C per 24 hours, wherein the range changes as a function of cancer profile 112. Nutrient amounts 132 may be calculated as heat maps (or similar mathematical arrangements), for instance using banding, where each datum of cancer profile 112 elicits a particular range of a particular nutrient amount 132 or set of amounts. In non-limiting illustrative examples, such a calculation may include querying for and retrieving a standard amount of water soluble vitamins for a healthy adult, for instance as described below in Table 1:

TABLE 1

| Nutrient | Amount |
| --- | --- |
| Vitamin C | 60 mg/day |
| Thiamin (B1) | 0.5 mg/1,000 kcal; 1.0 mg/day |
| Riboflavin (B2) | 0.6 mg/1,000 kcal; 1.2 mg/day |
| Niacin (B3) | 6.6 NE/1,000 kcal; 13 ND/day |
| Vitamin B6 | 0.02 mg/1 g protein; 2.2 mg/day |
| Vitamin B12 | 3 µg/day |
| Folic Acid | 400 µg/day |

Continuing in reference to FIG. 1, in reference to Table 1 above, wherein NE is niacin equivalent (1 mg niacin, or 60 mg tryptophan), mg (milligram), kcal (1000 kcal=1 Calorie), and µg (microgram). Computing device 104 may store and/or retrieve the above standard nutrient amounts, for instance in a database. The amounts may be re-calculated and converted according to a user's cancer profile 112. For instance, these amounts may relate to an average BMI, healthy adult male, for any range of calories, but may be adjusted according to unique user-specific cancer biomarkers 108. In non-limiting illustrative examples, an obese woman who is on a 1,400 Calorie/day diet, curated according to identified risk factors (cancer biomarkers 108) may need the above amounts recalculated according to such a diet, where some amounts may increase, some may decrease, and some may remain constant. For instance, if such a person were to suffer from leukemia, a particular increase among vitamin C may be calculated according to a weighting factor associated with leukemia; with colon cancer, vitamin C may increase by a different amount, but vitamin A from retinol sources (animal products) may need to decrease, and so on among many other cancer types.

Continuing in reference to FIG. 1, calculating nutrient amounts 132 may include deriving a weighting factor to adjust, or otherwise re-calculate, an amount. Weighting factor may be determined by computing device 104, for instance, by querying for vitamin amounts according to data inputs identified in the cancer profile 112. For instance in non-limiting illustrative examples, if cancer profile 112 indicates the presence of mutant forms of the BRCA1 and/or BRCA2 gene, vitamins involved in DNA-damage response pathways such as niacin and vitamin B6 may be increased in the diet by varying amounts. BRCA1/2 genes encode for proteins intimately involved in the DNA damage response (DDR). Mutant forms of DDR proteins may result in accumulated DNA damage that ultimately results in cancer formation. Prevention of cancer formation over the lifetime of the user in this manner may be achieved with supplementation of niacin, vitamin B6, among other nutrients such as biomolecules that can mitigate oxidative damage to DNA and alleviate the stress on the cell due to mutation in these genes. Although, niacin from organic sources (food items) may be superior from nonorganic sources (commercially-available supplements) from a bioavailability standpoint. Additionally, per-user pharmacokinetics, rates of metabolism and/or adsorption of niacin may differ user-to-user, which may negate the effectiveness of proscribing particular diet types and nutrition elements 120 to users. In such an instance, computing device 104 may account for such details using machine-learning to derive more specific nutrient amount 132 calculations and to more accurately calculate the amounts by which to increase/decrease niacin and vitamin B6 for the presence of the BRCA1/2 mutation.

Continuing in reference to FIG. 1, in non-limiting illustrative examples, such a machine-learning process may employ a machine-learning algorithm to derive per-user pharmacokinetics of vitamin B6. The machine-learning algorithm may accept an input of values including the total amount of protein consumed (in grams) and total amount of vitamin B6 consumed (in mg) per day in a diet, and what the serum levels of the vitamin B6 vitamer, pyridoxal-5-phosphate, over the course of a month, and derive the rates of metabolism, or how 'well' the user is obtaining the vitamin from nutrition elements 120 and adsorbing vitamin B6. In other words, the algorithm may derive a function (e.g. using linear regression, vector quantization, least squares, etc.) that describes the pharmacokinetics for that particular user regarding what amount of vitamin B6 consumed, per amount of dietary protein, results in what corresponding amount of bioactive vitamin compound, as measured by the blood vitamer from a biological extraction. Such a function, obtained from machine-learning, may then be used by computing device 104 with an input of the cancer profile 112, which enumerates the expression level (e.g. amount of BRCA1/2 RNA transcripts in tissue, protein expression level in the cell, etc.) and/or presence of BRCA1/2 mutation, to calculate an output which is a more accurate, customized, per-user nutrient amount 132 of vitamin B6. Persons skilled in the art may appreciate that this process may be repeated and completed for the full spectrum of nutrients, both required as part of a diet and not required as part of a diet.

Continuing in reference to FIG. 1, additionally, in non-limiting illustrative examples, computing device 104 may relate the concentrations of the metabolic products related to vitamins (e.g. vitamers), minerals, phytonutrients, antioxidative compounds, prodrugs, etc., to their effective concentrations in tissues related to various cancer categories 124 in cancer profile 112. For instance, computing device 104 may additionally search and retrieve data that relates the blood levels of the vitamin B6 vitamer, pyridoxal-5-phosphate, to the effective concentrations of vitamin B6 in breast tissue, which is particularly sensitive to aberrations in the DDR from BRCA1/2 mutations. Computing device 104 may store the values in a "look-up table", or graph a relationship as a mathematical function, among other ways of representing a data structure that relates the data identified in the search. Alternatively or additionally, computing device 104 may derive a function, for instance using machine-learning, which relates the concentration of the compound in a particular biological extraction, such as blood, to varying amounts in tissues such as breast tissue, liver, kidneys, etc. This may prove helpful in calculating nutrient amounts 132 as a function of user consumption to specific target nutrient amount 132 quantities within a particular organ/tissue according to the input data in the cancer profile 112.

Continuing in reference to FIG. 1, identifying the plurality of nutrition elements 120 according to the cancer category 124 may include training a machine-learning model. For instance and without limitation, training data for a machine-learning model may include nutrition elements 120 associated with, or correlated to, cancer categories 124, such as "colon cancer" nutrition elements 120, "glioblastoma" nutrition elements 120, etc. Training data may be used to train machine-learning model to derive an algorithm, which may automatedly return an output (plurality of nutrition elements 120) according to 1) cancer category 124 and 2) nutrient amounts 132 for every input (cancer profile 112). In such an instance, machine-learning model may include any machine-learning process, algorithm, and/or method, performed by a machine-learning module and computing device 104, as described in further detail below. Such a machine-learning model may include a classifier, which automatedly classifies nutrition elements 120 into categories according to cancer category 124 so that computing device 104 may "learn" which nutrition elements 120 to return as outputs according to relationships identified.

Continuing in reference to FIG. 1, calculating personalized nutrient amounts 132 may include generating training data using the plurality of nutrition elements 120 identified according to the cancer category 124. Curated nutritional elements 120 may include generating training data according to the plurality of nutrition elements 120 identified according to the cancer category 124. Generating training data may include retrieving the elements and constructing a file, data structure, with or without labels, identifying factors, or the like. Training data may originate from any source, as described above.

Continuing in reference to FIG. 1, calculating personalized nutrient amounts 132 may include training a nutrition machine-learning model 136 according to the training data, wherein training data includes a plurality of data entries that correlates the nutrition elements 120 for each cancer category 124 to nutrient amounts 132. Nutrition machine-learning model 136 may include any machine-learning model described herein, as performed by a machine-learning module, described in further detail below. Nutrition machine-learning model 136 may train with training data that includes nutrition elements 120 identified for each cancer category 124 to derive relationships in nutrient amounts 132 that relate to particular cancer category 124. For instance and without limitation, foods identified to be associated with particular cancers may reveal patterns in nutrients that have yet to be identified by physicians, cancer biologists, dieticians, and the like. Trained nutrition machine-learning model 136 may generate a function (or series of functions) which describe alterations to nutrient amounts 132 calculated directly from cancer profile 112, prior to classification to cancer category 124. In non-limiting illustrative examples, it may be shown that fiber content, which is oftentimes classically reported in a generic sense as "carbohydrates", is important for particular gastric cancers and colon cancers. Patterns may identify that plant-based diets, supplemented with particular bacterial species of probiotics may result in personalized nutrient amounts 132 for cancer profiles 112 classified to those cancer categories 124.

Continuing in reference to FIG. 1, calculating nutrient amounts 132 may include calculating nutrient amounts 132 as a function of the nutrition machine learning model 136 and the cancer category 124. Trained nutrition machine learning model 136 may accept an input of cancer profile 112 (and associated cancer category 124) to output nutrient amounts 132. Nutrient amounts 132 may be calculated using a variety of functions, systems of equations, and the like, derived from mathematical relationships and/or heuristics identified in training data, for instance from nutrition elements 120 identified from cancer categories 124. Persons skilled in the art may appreciate that each cancer category 124, of 100+ different types of cancers, may have a unique algorithm for identifying nutrient amounts 132, of the 100's of distinct nutrients identified. For instance and without limitation, each cancer type, tissue/organ type, cancer stage, age of person, cancer biomarker 108, cancer profile 112, etc., may elicit a different mathematical equation for calculating vitamin C. Wherein, vitamin C is one of many water-soluble vitamins, and that each vitamin of that class may have a different equation associated with calculating nutrient amounts 132. Each equation may be derived by nutrition machine learning model 136 according to the training data. Additionally, each user's specific pharmacokinetics, current dietary patterns, and the like, may add a unique step in the calculation, wherein the calculated nutrient amount 132 is further personalized.

Continuing in reference to FIG. 1, identifying the plurality of nutrition elements 120 includes identifying the nutrition elements 120 according to the cancer category 124. Identifying nutrition element 120 according to cancer category 124 may include querying, for instance using a web browser and the Internet, for foods, supplements, bioactive ingredients, and the like, which are correlated with a particular cancer category 124. For instance and without limitation, computing device 104 may organize a search for foods intended for "colon cancer", wherein an entire diet may be crafted around target nutrient amounts 132 and the categorization of the cancer profile 112 to "colon cancer". In such an example, the nutrition elements 120 are outputs generated from an input search criteria of "colon cancer". The output elements become "personalized" as they are arranged into daily, weekly, monthly, etc., individual meals and/or meal schedule according to a user's particular calculated nutrient amounts 132. The cancer category 124 may serve as a filtering step, wherein a search is guided by the cancer profile 112 as it was classified to a cancer type.

Continuing in reference to FIG. 1, identifying the plurality of nutrition elements 120 includes identifying, as a function of the plurality of nutrient amounts 132, the plurality of nutrition elements 120, wherein the plurality of nutrition elements 120 are intended to prevent cancer as a function of the cancer category 124. Cancer profile 112 may be associated with user that does not currently have a cancer belonging to cancer category 124. In such an instance, nutrition elements 120 may be "personalized" to an individual in that they are intended to prevent, as described above, cancer in that individual. Nutrition element 120 may prevent cancer in that they provide a nutrient intended to meet individualized, calculated nutrient amounts 132. Nutrient element 120 may prevent cancer in addressing the accumulation of heavy metals, such as lead, mercury, and cadmium, in a user. Nutrition element 120 may prevent cancer in addressing risk factors associated with the development of cancer such as exposure to asbestos, glass dust, fibers, and other particulate matter. Nutrition element 120 may include foods and supplements intended to address genetic and cancer biomarker 108 issues that are unique to each individual. "Curating" nutritional elements 120, as used in this disclosure, is a process of combining ingredients and/or nutrients according to calculated nutrient amounts 132. Curated nutritional elements 120 may include combining ingredients such as spices, plant-based materials, animal products, probiotic cultures, and the like, to result in a custom nutritional element 120, such as a particular "health shake", unique dish, or the like.

Continuing in reference to FIG. 1, computing device 104 is configured to identify, as a function of the calculated nutrient amounts 132, the plurality of nutrition elements 120, wherein the plurality of nutrition elements 120 are intended to address a datum in the cancer profile 112. Nutrition elements 120, "intended to address a datum in the cancer profile 112," may refer to the process(es) of cancer treatment and/or prevention. "Cancer treatment," as used in this disclosure, is the amelioration of cancer symptomology; such as nutrition elements 120 intended for a person currently diagnosed with cancer and completing XRT treatment (radiation therapy) and/or chemotherapy regimen. "Cancer prevention," as used in this disclosure, is the reduction in risk for cancer; cancer prevention may include specifically curated nutrition elements 120 according to nutrient amount 124 that contain predetermined relationship regarding the lifetime risk of cancer, wherein the risk is decreased if nutrient targets are achieved.

Continuing in reference to FIG. 1, computing device 104 may identify the plurality of nutrition elements 120 by using nutrient amount 124 as an input and generating combinations, lists, or other aggregates of nutrition elements 120 necessary to achieve nutrient amount 124. For instance, computing device 104 may use a template nutrient amount 124 of '200 mg vitamin C' and build a catalogue of nutritional elements 120 until the 200 mg vitamin C value is obtained. Computing device 104 may perform this task by querying for food items, for instance from a menu, grocery list, or the like, retrieving the vitamin C content, and subtracting the value from the nutrient amount 124. In non-limiting illustrative examples, computing device 104 may identify orange juice (90 mg vitamin C/serving; 200 mg−90 mg=110 mg) for breakfast, Brussel sprouts (50 mg vitamin C/serving; 110 mg−50 mg=60 mg) for lunch, and baked potato (20 mg vitamin C/serving) and spicy lentil curry (40 mg vitamin C/serving; 60 mg−(20 mg+40 mg)=0 mg) for dinner. In such an example, computing device 104 may search according to a set of instructions (e.g. food preferences, allergies, restrictions, etc.) present in a cancer profile 112, provided by a physician, user, or the like, and subtract each identified nutrition element 120 nutrient amount from nutrient amount 124 until a combination of nutritional elements 120 that represents a solution is found. Once a solution is found, computing device 104 may generate a file of nutrition elements 120 and store in a database, as described in further detail below.

Continuing in reference to FIG. 1, generating combinations of nutrition elements 120 to achieve nutrient amounts 132 may include generating an objective function. An "objective function," as used in this disclosure, is a mathematical function that may be used by computing device 104 to score each possible combination of nutrition elements 120, wherein the objective function may refer to any mathematical optimization (mathematical programming) to select the 'best' element from a set of available alternatives. Selecting the 'best' element from a set of available alternatives may include a combination of nutrition elements 120 which achieves the nutrient amounts 132 in addressing cancer profile 112 in a user.

Continuing in reference to FIG. 1, an objective function may include performing a greedy algorithm process. A "greedy algorithm" is defined as an algorithm that selects locally optimal choices, which may or may not generate a globally optimal solution. For instance, computing device 104 may select combinations of nutrition elements 120 so that values associated therewith are the best value for each category. For instance, in non-limiting illustrative example, optimization may determine the combination of the most efficacious 'serving size', 'timing of consumption', 'probiotic product', 'vegetable', etc., categories to provide a combination that may include several locally optimal solutions but may or may not be globally optimal in combination.

Still referring to FIG. 1, objective function may be formulated as a linear objective function, which computing device 104 may solve using a linear program, such as without limitation, a mixed-integer program. A "linear program," as used in this disclosure, is a program that optimizes a linear objective function, given at least a constraint; a linear program may be referred to without limitation as a "linear optimization" process and/or algorithm. For instance, in non-limiting illustrative examples, a given constraint might be a metabolic disorder of a user (e.g. lactose intolerance, poor absorption, food allergy, user preference, etc.), and a linear program may use a linear objective function to calculate combinations, considering how these limitations effect combinations. In various embodiments, system 100 may determine a set of instructions towards addressing a subject's cancer profile 112 that maximizes a total cancer prevention score subject to a constraint that there are other competing objectives. For instance, if achieving one nutrient amount 124 by selecting from each nutrition element 120 may result in needing to select a second nutrition element 120, wherein each may compete in cancer prevention (e.g. adopting two or more diet types simultaneously may not be feasible, a vegan option and a non-vegan option, etc.). A mathematical solver may be implemented to solve for the set of instructions that maximizes scores; mathematical solver may be implemented on computing device 104 and/or another device in system 100, and/or may be implemented on third-party solver.

With continued reference to FIG. 1, objective function may include minimizing a loss function, where a "loss function" is an expression an output of which a process minimizes to generate an optimal result. For instance, achieving nutrient amounts 132 may be set to a nominal value, such as '100', wherein the objective function selects elements in combination that reduce the value to '0', wherein the nutrient amounts 132 are '100% achieved'. In such an example, 'maximizing' would be selecting the combination of nutrition elements 120 that results in achieving nutrient amounts 132 by minimizing the difference. As a non-limiting example, computing device 104 may assign variables relating to a set of parameters, which may correspond to cancer prevention components, calculate an output of mathematical expression using the variables, and select an objective that produces an output having the lowest size, according to a given definition of "size." Selection of different loss functions may result in identification of different potential combinations as generating minimal outputs, and thus 'maximizing' efficacy of the combination.

Continuing in reference to FIG. 1, computing device 104 may use calculated nutrient amounts 132 from nutrition machine learning model 136 to determine nutrition elements 120 more precisely. For instance, computing device 104 may retrieve a variety of nutrition elements 120 which contain particular vitamins, minerals, anti-inflammatory molecules, phytonutrients, antioxidants, bioactive molecules, and the like, which do not violate any other cancer prevention information associated with cancer profile 112. Computing device 104 may mix-and-match nutrition elements 120 to arrive at a particular calorie amount, or range of calories, while achieving nutrient amounts 132.

Continuing in reference to FIG. 1, computing device 104 is configured to generate, using the plurality of nutrition elements 120, the cancer alleviation nourishment plan. A "nourishment plan," as used in this disclosure, is a collection of nutrient amounts 132 and nutrition elements 120 organized into a frequency (timing) and magnitude (serving size) schedule. Nourishment plan 140 may include gathering, classifying, or otherwise categorizing nutrient amounts 132, nutrition elements 120 lists, or the like, which incorporates cancer-specific recommendations. For instance, nutrition elements 120 may be scored with a numerical score scale that associates a meal, beverage, supplement, etc., with preventing cancer, benefit to cancer patient, and the like. Nourishment plan 140 may include selecting nutrition elements 120 according to a threshold score, where items above are selected and arranged. Threshold score may include a daily threshold, wherein nutrition elements 120 are selected each day according to the threshold; and threshold may include a numerical value relating to cancer prevention, nutrient amount 132, among other outputs of system 100 described herein. Determining nourishment plan 140 may include machine-learning. For instance, training a machine-learning model to identify a scoring rubric for building the nourishment plan 140 based on some criteria such as cancer prevention, achieving remission, efficacy for helping maintain remission, among other criteria. Nourishment plan 140 may relate specific cancers to specific nutrients of interest and provide nutrition element 120 scheduling times and serving sizes for each meal. Nourishment plan 140 may differ from one user to the next according to the magnitude of the disease outline (cancer category 124 and cancer profile 112).

Continuing in reference to FIG. 1, nourishment plan 140 may include a recommended nutrition plan and a recommended supplement plan that at least addresses cancer biomarker 108, mitigates symptoms, side-effects, etc. Nourishment plan 140 may contain a plan with timing of meals, calorie amounts, vitamin amounts, mineral amounts, etc. Nourishment plan 140 may include food items combined with a supplement of non-food items. Nourishment plan 140 may be presented as a function of reversing, treating, and/or preventing cancer for non-cancer patients, for instance an otherwise healthy person to reduce their lifelong risk of cancer. The lifelong risk of cancer may be enumerated in nourishment score 148. Such a score may increase with participation in nourishment plan 140 and/or decrease by falling short of nutrient amounts 132. Nourishment plan 140 may include one or more treatment plans that incorporate, for instance and without limitation, large quantities of acai berry and other antioxidants, phytonutrients, and bioactive ingredients to prevent oxidative damage that leads to the presence of free radicals. Nourishment plan 140 may be focused on achieving remission for a cancer patient, where nourishment score 148 is tied to progression to remission, increasing with achieving remission, and again increasing with each remission milestone.

Continuing in reference to FIG. 1, generating the cancer alleviation nourishment plan 140 may include generating a nourishment plan classifier using a nourishment classification machine-learning process to classify the plurality of nutrient amounts 132 to the plurality of nutrition elements 120, and outputting the plurality of nutrition elements as a function of the nourishment plan classifier. Nourishment plan classifier 144 may include any classifier as described above generated by a classification machine-learning process using training data, as described herein, performed by a machine-learning module as described in further detail below. Training data for nourishment plan classifier 144 may include sets of data entries that include nutrition elements 120 (foods, supplements, recipes, etc.) that are correlated to nutrient amounts 132 of vitamins, minerals, phytonutrients, antioxidants, and the like, that classifier may be trained to automatedly locate, sort, and output nutrition elements 120 according to a user's cancer category 124 and the nutrient amounts 132 they should receive. Such training data may originate via a database, the Internet, research repository, and the like, as described above for training data for other machine-learning processes. Nourishment plan classifier 144 may accept an input of nutrient amounts 132 and output a plurality of nutrition elements 120 with associated frequency (timing) and magnitude (serving size) schedule according to relationships between nutrition elements 120 and nutrient amounts 132. For instance and without limitation, nourishment plan classifier 144 may contain relationships between individual fruits and vegetables, that when more vegetables are selected, certain fruits may not be necessary to schedule within the same timeframe (day, meal, etc.). Such a classification process may determine a function, system of equations, and the like, which can be solved for in determining which nutrition elements 120 (fruits, vegetables, meats, dairy, grains, etc.) are useful to obtaining the nutrient amounts 132, while not missing some lower limits of nutrient amounts 132 (trace elements) and not exceeding upper limits for other nutrient amounts 132 (calories).

Continuing in reference to FIG. 1, generating the cancer alleviation nourishment plan 140 may include generating a nourishment score, wherein the nourishment score reflects the level of user participation in the cancer alleviation nourishment plan 140. A "nourishment score," as used in this disclosure, reflects the level of user participation in the cancer alleviation nourishment plan. Nourishment score may include a numerical value, metric, parameter, and the like, described by a function, vector, matrix, or any other mathematical arrangement. Nourishment score 148 may include enumerating a user's current nourishment as it relates to cancer alleviation. Generating nourishment score 148 may include using a machine-learning process, algorithm, and/or model to derive a numerical scale along which to provide a numerical value according to a user's cancer profile 112 and participation in nourishment plan 140 generated from cancer profile 112. For instance, such a machine-learning model may be trained with training data, wherein training data contains data entries of nutrient amounts 132 correlated to cancer prevention. Such a machine-learning model with said training data may be used by computing device 104 to relate the consumption of particular foods in nourishment plan 140, to achieving some level of nutrient amount 132, and how the nutrient amount 132 relates to cancer alleviation, achieving remission, maintaining remission, etc.

Continuing in reference to FIG. 1, in non-limiting illustrating examples, falling short of vitamin E and vitamin K nutrient amounts 132, may have a particular effect on nourishment score 148 for an individual who has been classified to "skin cancer" cancer category 124. Where, chronically falling short of the nutrient amount 132 results in a (−3 score) each month but falling within the nutrient amount 132 range for those two nutrients affords (+1 score for each) every month; the target amount for the preceding month may dictate the score change for each subsequent month. In such a case, a machine-learning model may derive an algorithm which dictates the amount to increase/decrease nourishment score 148 for that particular cancer category 124 according to the nutrient amounts 132. In this case, the machine-learning model is trained to identify the relationship between nutrient amounts 132 and effect on cancer prevention to derive an equation that relates scoring criteria. The score is then calculated using the model and nutrition data as an input. "Nutrition data," as used in this disclosure, is data describing consumption by the user. Consumption by the user may include amounts and identities of nutrition elements 120. In this way, system 100 may calculate a nourishment score 148 as a function of a user's participation in nourishment plan 140, where nourishment score 148 is updated with each nutrition element 120 consumed by user.

Continuing in reference to FIG. 1, generating the cancer alleviation nourishment plan 140 may include calculating a change in incidence of cancer as a function of adhering to nourishment plan 140. Calculating a change in incidence of cancer may include receiving nutritional input from a user, for instance and without limitation, as described in Ser. No. 16/911,994, filed Jun. 25, 2020, titled "METHODS AND SYSTEMS FOR ADDITIVE MANUFACTURING OF NUTRITIONAL SUPPLEMENT SERVINGS," the entirety of which is incorporated herein by reference. System 100 may receive nutritional input from a user. "Nutritional input," as used in this disclosure, is an amount of a nutrient consumed by a user. Nutritional input, for instance and without limitation, may include food items that have associated nutrition facts, wherein computing device 104 may calculate, weight, or otherwise modify, the nutritional input from the user (e.g. with a weighting factor). This results in accurate, per-user nutritional input. That nutritional input can be used to determine (for instance using subtraction) what amount of target nutrient amounts 132 summarized in the nourishment plan 140 the user is consuming. The adherence to the nourishment plan 140 is calculated from that, and the incidence of cancer may be determined from the adherence to the nourishment plan. Nutritional input of a user may include a designation of any nutrition elements 120 user may have consumed. Nutritional elements 120 may have nutrient amounts 132 associated therewith, which may be applied to a user's current cancer profile 112, cancer category 124, malignant parameters, and the like. Applying the nutrient amounts 132 may include calculated a difference in nourishment score 148. Applying the nutrient amounts 132 may include calculating a change in cancer risk, likelihood, or incidence as a function of achieving nutrient amounts 132, as described above, which may be enumerated in nourishment score 148.

Continuing in reference to FIG. 1, generating the cancer alleviation nourishment plan 140 may include receiving a user preference regarding the plurality of nutrition elements 120, and modifying the plurality of nutrition elements 120 as a function of the user preference. A "user preference," as used in this disclosure, is a user input that designates a preference related to at least a nutrition element 120. User preference 152 may include designations of nutrition elements 120 to avoid and/or include such as particular food groups, condiments, spices, dietary restrictions such as no animal products, cuisine type such as Mediterranean foods, time of day for eating such as fasting before 10 am, etc. In this way, computing device 104 may accept an input of user preference 152 filter, sort, classify, or otherwise modify the data structure of nutrition elements 120 and schedule the nutrition elements 120 into nourishment plan 140 in a custom, per-user manner. Computing device 104 may modify the plurality of nutrition elements 120 as a function of the user preference 144, for instance by providing recipes with steps omitted, new steps added, or entirely new recipes altogether utilizing the same or different nutrition elements 120. Computing device 104 may modify the plurality of nutrition elements 120 as a function of the user preference 144 by generating a new file, based on the preference, and storing and/or retrieving the file from a database, as described in further detail below.

Figure 2:
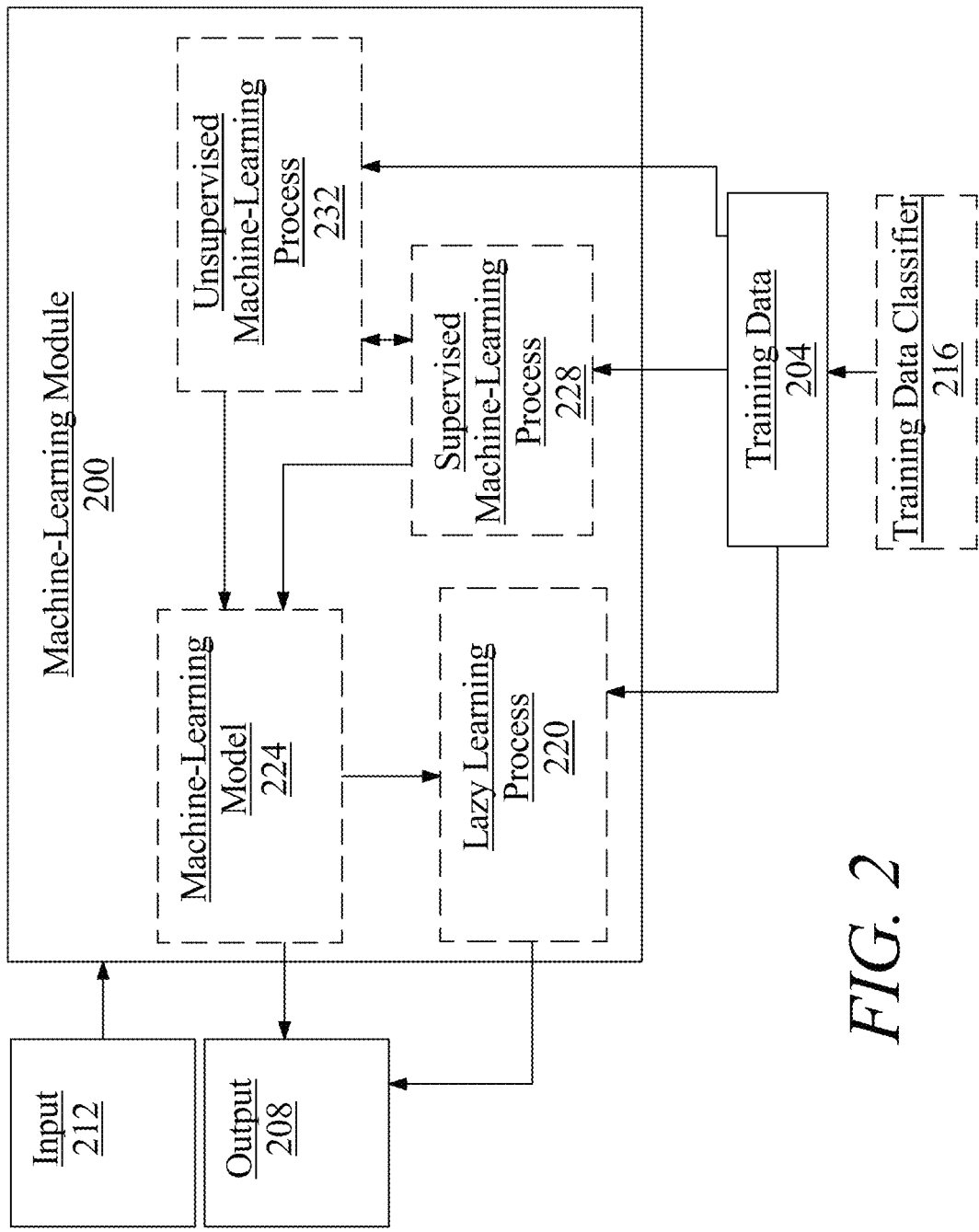
FIG. 2 is a block diagram illustrating a machine-learning module.

Referring now to FIG. 2, an exemplary embodiment of a machine-learning module 200 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 204 to generate an algorithm that will be performed by a computing device/module to produce outputs 208 given data provided as inputs 212; this is in contrast to a non-machine learning software program where the commands to be executed are determined in advance by a subject and written in a programming language.

Still referring to FIG. 2, "training data," as used herein, is data containing correlations that a machine-learning process may use to model relationships between two or more categories of data elements. For instance, and without limitation, training data 204 may include a plurality of data entries, each entry representing a set of data elements that were recorded, received, and/or generated together; data elements may be correlated by shared existence in a given data entry, by proximity in a given data entry, or the like. Multiple data entries in training data 204 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 204 according to various correlations; correlations may indicate causative and/or predictive links between categories of data elements, which may be modeled as relationships such as mathematical relationships by machine-learning processes as described in further detail below. Training data 204 may be formatted and/or organized by categories of data elements, for instance by associating data elements with one or more descriptors corresponding to categories of data elements. As a non-limiting example, training data 204 may include data entered in standardized forms by persons or processes, such that entry of a given data element in a given field in a form may be mapped to one or more descriptors of categories. Elements in training data 204 may be linked to descriptors of categories by tags, tokens, or other data elements; for instance, and without limitation, training data 204 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 2, training data 204 may include one or more elements that are not categorized; that is, training data 204 may not be formatted or contain descriptors for some elements of data. Machine-learning algorithms and/or other processes may sort training data 204 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 204 to be made applicable for two or more distinct machine-learning algorithms as described in further detail herein. Training data 204 used by machine-learning module 200 may correlate any input data as described in this disclosure to any output data as described in this disclosure.

Further referring to FIG. 2, training data may be filtered, sorted, and/or selected using one or more supervised and/or unsupervised machine-learning processes and/or models as described in further detail herein; such models may include without limitation a training data classifier 216. Training data classifier 216 may include a "classifier," which as used in this disclosure is a machine-learning model as defined herein, such as a mathematical model, neural net, or program generated by a machine learning algorithm known as a "classification algorithm," as described in further detail herein, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 200 may generate a classifier using a classification algorithm, defined as a process whereby a computing device and/or any module and/or component operating thereon derives a classifier from training data 204. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 216 may classify elements of training data to elements that characterizes a sub-population, such as a subset of cancer biomarkers 108 (such as gene expression patterns as it relates to cancer profile 112) and/or other analyzed items and/or phenomena for which a subset of training data may be selected.

Still referring to FIG. 2, machine-learning module 200 may be configured to perform a lazy-learning process 220 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of predictions may be performed to cover an initial heuristic and/or "first guess" at an output and/or relationship. As a non-limiting example, an initial heuristic may include a ranking of associations between inputs and elements of training data 204. Heuristic may include selecting some number of highest-ranking associations and/or training data 204 elements, such as classifying cancer biomarker 108 elements to cancer profile 112 elements and assigning a value as a function of some ranking association between elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail herein.

Alternatively or additionally, and with continued reference to FIG. 2, machine-learning processes as described in this disclosure may be used to generate machine-learning models 224. A "machine-learning model," as used in this disclosure, is a mathematical and/or algorithmic representation of a relationship between inputs and outputs, as generated using any machine-learning process including without limitation any process as described above and stored in memory; an input is submitted to a machine-learning model 224 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 224 may be generated by creating an artificial neural network, such as a convolutional neural network comprising an input layer of nodes, one or more intermediate layers, and an output layer of nodes. Connections between nodes may be created via the process of "training" the network, in which elements from a training data 204 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. A machine-learning model may be used to derive numerical scales for providing numerical values to cancer profile 112 and/or nourishment score 148, etc., as described above, to "learn" the upper and lower limits to the numerical scale, the increments to providing scoring, and the criteria for increasing and decreasing elements encompassed in the cancer profile 112 and/or nourishment score 148, etc. A machine-learning model may be used to "learn" which elements of cancer biomarkers 108 have what effect on cancer profile 112, and which elements of cancer profile 112 are affected by particular nutrition elements 120 and the magnitude of effect, etc. The magnitude of the effect may be enumerated and provided as part of system 100, where nutrition elements 120 are communicated to user for their cancer preventative properties.

Still referring to FIG. 2, machine-learning algorithms may include at least a supervised machine-learning process 228. At least a supervised machine-learning process 228, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include a cancer profile 112 (potentially classified into cancer categories 124), as described above as inputs, nutrient element 120 outputs, and a ranking function representing a desired form of relationship to be detected between inputs and outputs; ranking function may, for instance, seek to maximize the probability that a given input (such as nutrient amounts 132) and/or combination of inputs is associated with a given output (nourishment plan 140 that incorporate nutrient elements 120 to achieve nutrient amounts 132 that are 'best' for cancer category 124) to minimize the probability that a given input is not associated with a given output, for instance finding the most suitable times to consume meals, and what the meals should be, etc. Ranking function may be expressed as a risk function representing an "expected loss" of an algorithm relating inputs to outputs, where loss is computed as an error function representing a degree to which a prediction generated by the relation is incorrect when compared to a given input-output pair provided in training data 204. Persons skilled in the art, upon reviewing the entirety of this disclosure, will be aware of various possible variations of at least a supervised machine-learning process 228 that may be used to determine relation between inputs and outputs. Supervised machine-learning processes may include classification algorithms as defined above.

Further referring to FIG. 2, machine learning processes may include at least an unsupervised machine-learning process 232. An unsupervised machine-learning process 232, as used herein, is a process that derives inferences in datasets without regard to labels; as a result, an unsupervised machine-learning process 232 may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 2, machine-learning module 200 may be designed and configured to create a machine-learning model 224 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 2, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Still referring to FIG. 2, models may be generated using alternative or additional artificial intelligence methods, including without limitation by creating an artificial neural network, such as a convolutional neural network comprising an input layer of nodes, one or more intermediate layers, and an output layer of nodes. Connections between nodes may be created via the process of "training" the network, in which elements from a training data 204 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using training data 204.

Figure 3:
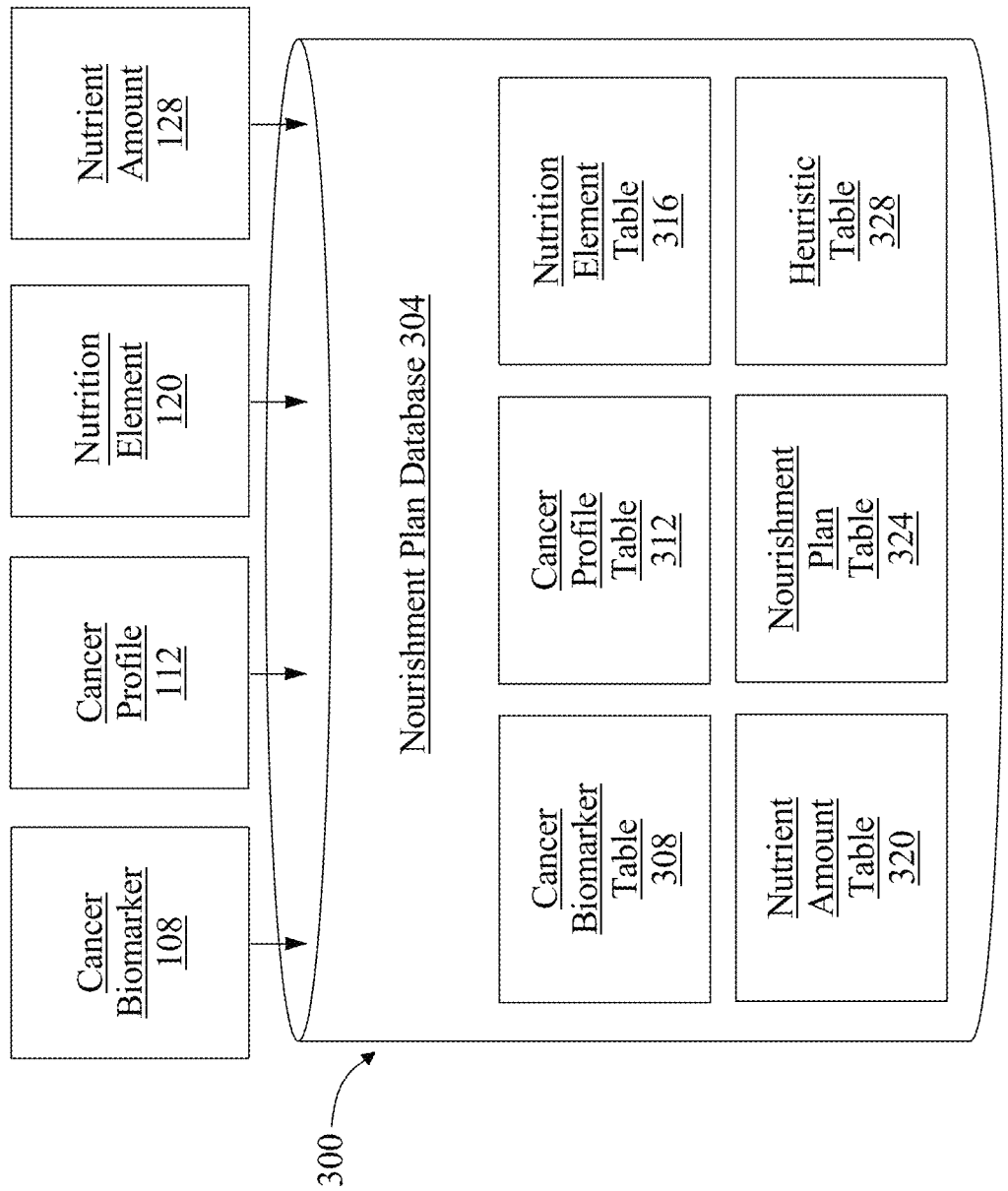
FIG. 3 is a block diagram of a cancer nourishment plan database.

Referring now to FIG. 3, a non-limiting exemplary embodiment 300 of a nourishment plan database 304 is illustrated. Cancer biomarker 108 for a plurality of subjects, for instance for generating a training data classifier 216, may be stored and/or retrieved in nourishment plan database 304. Cancer biomarker 108 data from a plurality of subjects for generating training data 204 may also be stored and/or retrieved from a nourishment plan database 304. Computing device 104 may receive, store, and/or retrieve training data 204, wearable device data, physiological sensor data, biological extraction data, and the like, from nourishment plan database 304. Computing device 104 may store and/or retrieve nutrient machine-learning model 116, among other determinations, I/O data, models, and the like, in nourishment plan database 304.

Continuing in reference to FIG. 3, nourishment plan database 304 may be implemented, without limitation, as a relational database, a key-value retrieval database such as a NOSQL database, or any other format or structure for use as a database that a person skilled in the art would recognize as suitable upon review of the entirety of this disclosure.

Nourishment plan database 304 may alternatively or additionally be implemented using a distributed data storage protocol and/or data structure, such as a distributed hash table and the like. Nourishment plan database 304 may include a plurality of data entries and/or records, as described above. Data entries in a nourishment plan database 304 may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a database may store, retrieve, organize, and/or reflect data and/or records as used herein, as well as categories and/or populations of data consistent with this disclosure.

Further referring to FIG. 3, nourishment plan database 304 may include, without limitation, cancer biomarker table 308, cancer profile table 312, nutrition element table 316, nutrient amount table 320, nourishment plan table 324, and/or heuristic table 328. Determinations by a machine-learning process, machine-learning model, ranking function, and/or classifier, may also be stored and/or retrieved from the nourishment plan database 304. As a non-limiting example, nourishment plan database 304 may organize data according to one or more instruction tables. One or more nourishment plan database 304 tables may be linked to one another by, for instance in a non-limiting example, common column values. For instance, a common column between two tables of nourishment plan database 304 may include an identifier of a submission, such as a form entry, textual submission, accessory device tokens, local access addresses, metrics, and the like, for instance as defined herein; as a result, a search by a computing device 104 may be able to retrieve all rows from any table pertaining to a given submission or set thereof. Other columns may include any other category usable for organization or subdivision of data, including types of data, names and/or identifiers of individuals submitting the data, times of submission, and the like; persons skilled in the art, upon reviewing the entirety of this disclosure, will be aware of various ways in which data from one or more tables may be linked and/or related to data in one or more other tables.

Continuing in reference to FIG. 3, in a non-limiting embodiment, one or more tables of a nourishment plan database 304 may include, as a non-limiting example, a cancer biomarker table 308, which may include categorized identifying data, as described above, including genetic data, epigenetic data, microbiome data, physiological data, biological extraction data, and the like. Cancer biomarker table 308 may include cancer biomarker 108 categories according to gene expression patterns, SNPs, mutations, enzyme specific activity and concentration, phosphorylation data, proteasomal degradation data, data concerning metabolism of nutrition elements 120, pharmacokinetics, nutrient absorption, etc., categories, and may include linked tables to mathematical expressions that describe the impact of each cancer biomarker 108 datum on cancer profile 112, for instance threshold values for gene expression, etc., as it relates to cancer, cancer category 124, etc. One or more tables may include cancer profile table 312, which may include data regarding cancer biomarker 108, thresholds, scores, metrics, values, categorizations, and the like, that system 100 may use to calculate, derive, filter, retrieve and/or store current cancer levels, cancer types, likelihood of currently having a malignancy, probability of malignancy, metastasis, and the like. One or more tables may include nutrition element table 316, which may include data on nutrition elements 120 for instance classified to cancer category 124, classified to data from alike subjects with similar cancer biomarker 108, cancer profile 112, and the like, that system 100 may use to calculate, derive, filter, retrieve and/or store nutrition elements 120. One or more tables may include nutrient amount table 320, which may include functions, model, equations, algorithms, and the like, using to calculate or derive nutrient amounts 132 relating to cancer profile 112 and/or cancer category 124, may include nutrient amounts 132 organized by nutrient, nutrient classification, age, sex, cancer severity, remission, etc. One of more tables may include a nourishment plan table 324, which may include nutrition element 120 identifiers, serving sizes, times associated with nutrition elements 120, regarding times to eat, identifiers of meals, recipes, ingredients, schedules, diet types, and the like. One or more tables may include, without limitation, a heuristic table 328, which may organize rankings, scores, models, outcomes, functions, numerical values, scales, arrays, matrices, and the like, that represent determinations, probabilities, metrics, parameters, values, and the like, include one or more inputs describing potential mathematical relationships, as described herein.

Referring now to FIGS. 4A and 4B, a non-limiting exemplary embodiment 400 of a cancer profile 112 is illustrated. Cancer profile 112 may include a variety of cancer biomarker 108 categories, for instance 22 distinct categories, as shown in FIGS. 4A and 4B. each cancer biomarker 108 may be assigned a value, such as an arbitrary value, where some cancer biomarkers 108, such as those shaded in light grey, may relate to absolute scales from [0, x], where x is a maximal value and the range of values for the cancer biomarker 108 cannot be below a 'zero amount'. Some cancer biomarkers 108, such as those shaded in dark grey, may relate to gene expression levels, wherein, the cancer biomarker 108 is enumerated as a 'box plot' that illustrates the range of expression in a population of users organized according to, for instance tissue type. In such an example, the dashed line may relate to a 'normal threshold' above which is elevated gene expression, below which is decreased expression level. Each cancer biomarker 108 may have associated with it a numerical score, or some other identifying mathematical value that computing device 104 may assign. Persons skilled in the art may appreciate that for each user, any number of cancer biomarkers 108 may be enumerated and assigned a value according to cancer profile machine-learning model 116. Cancer profile 112 may be graphed, or otherwise displayed, according to the enumeration by cancer profile machine-learning model 116. Each bar of the bar graph, or combinations of bar graph categories, may instruct a classification of a user's cancer profile 112 to a cancer category 124.

Still referring now to FIGS. 4A and 4B, in non-limiting exemplary illustrations cancer profile 112 may be classified to a cancer category 124. Some and/or all of the cancer biomarkers 108 summarized in cancer profile 112 may be used to classify an individual to a particular cancer category 124. For instance, as shown in FIG. 4B, ten of the 22 cancer biomarker 108 categories may be used to classify cancer profile 112 to one or more cancer categories 124. Alternatively or additionally, cancer profile machine-learning model 116 may be trained to assign cancer biomarker 108 to a cancer category 124, wherein computing device 104 may know the identity of cancer category 124 according to which cancer category 124 has the most identifying data points.

Figure 5:
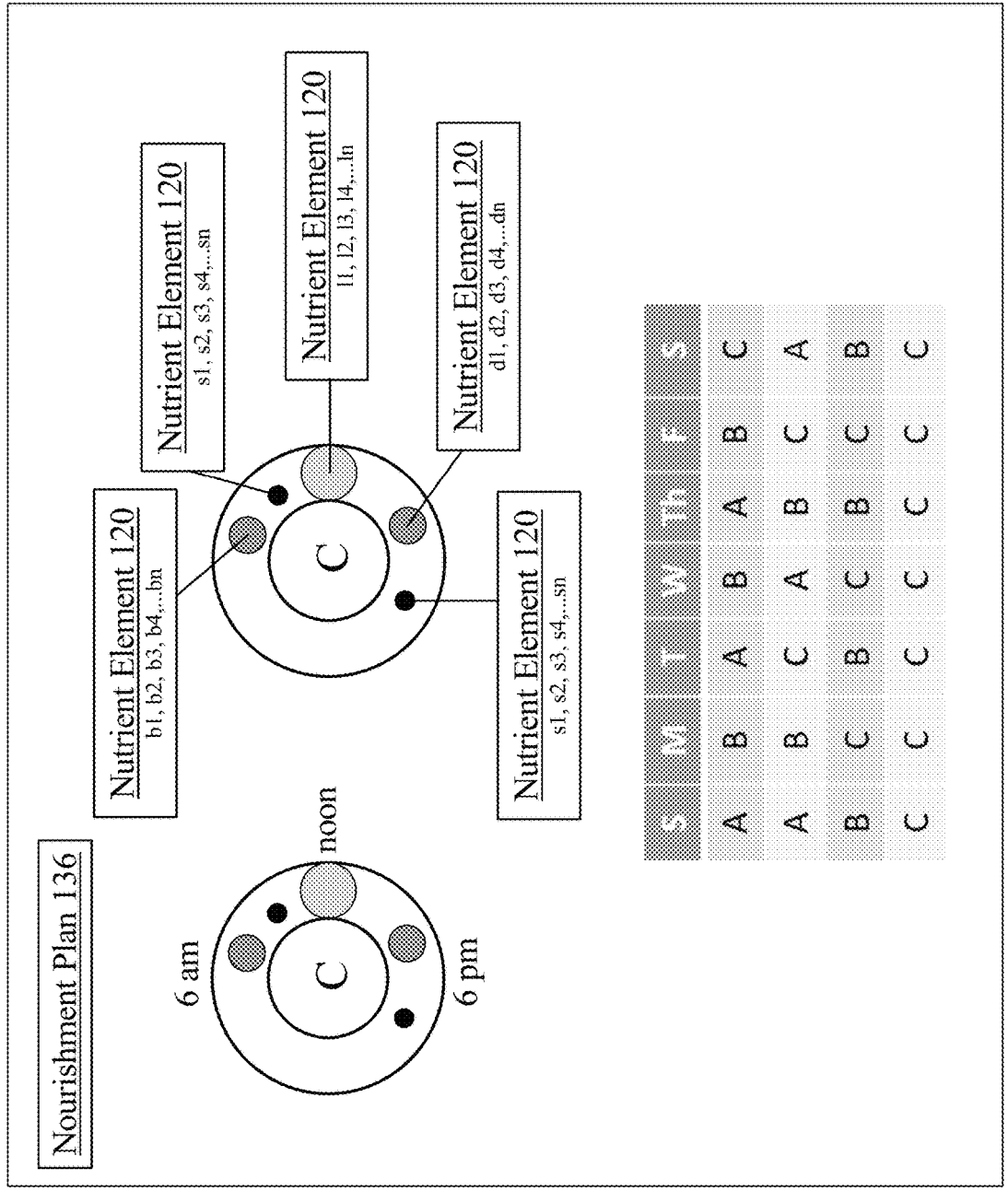
FIG. 5 is a diagrammatic representation of a cancer alleviation nourishment plan.

Referring now to FIG. 5, a non-limiting exemplary embodiment 500 of a cancer alleviation nourishment plan 140 is illustrated. Nourishment plan 140 may include a schedule for arranging nutrition elements 120, according to for instance a 24-hour timetable, as designated on the left, where consumption is planned along a user's typical day-night cycle, beginning at ~6 am until just after 6 pm. Nutrition element 120 may include breakfast (denoted as mid-sized dark grey circle), which may correspond to a file of breakfast-related plurality of nutrition elements 120 (denoted b1, b2, b3, b4 . . . bn, to the nth breakfast item). Nutrition element 120 may include snacks eaten throughout the day to, for instance achieve nutrient amounts 132 missing from meals (denoted as small black circles), which may correspond to a file of snacking-related plurality of nutrition elements 120 (denoted s1, s2, s3, s4 . . . sn, to the nth snacking item). Nutrition element 120 may include dinner (denoted as large-sized light grey circle), which may correspond to a file of dinner-related plurality of nutrition elements 120 (denoted d1, d2, d3, d4 . . . dn, to the nth dinner item). Nourishment plan 140 may include a variety of diets, as denoted in the monthly schedule at the bottom, Sunday through Saturday. Nourishment plan 140 'C' is shown, which may be an idealistic goal for user to achieve by the end of the month, where nourishment plan 'A' and 'B' are intermediate plans intended to wean user to the 'ideal' plan. Nutrition elements 120 classified by 'meal type' may be further modified by 'A' and 'B' according to user preferences 148 collected by computing device 104 throughout the process. Circle sizes, denoting nutrition element 120 classes may relate to portion sizes, which are graphed along the circle corresponding to the times they are expected to be consumed. User may indicate which nutrition element 120 from each category was consumed, and when it was consumed, to arrive at nourishment score 148.

Figure 6:
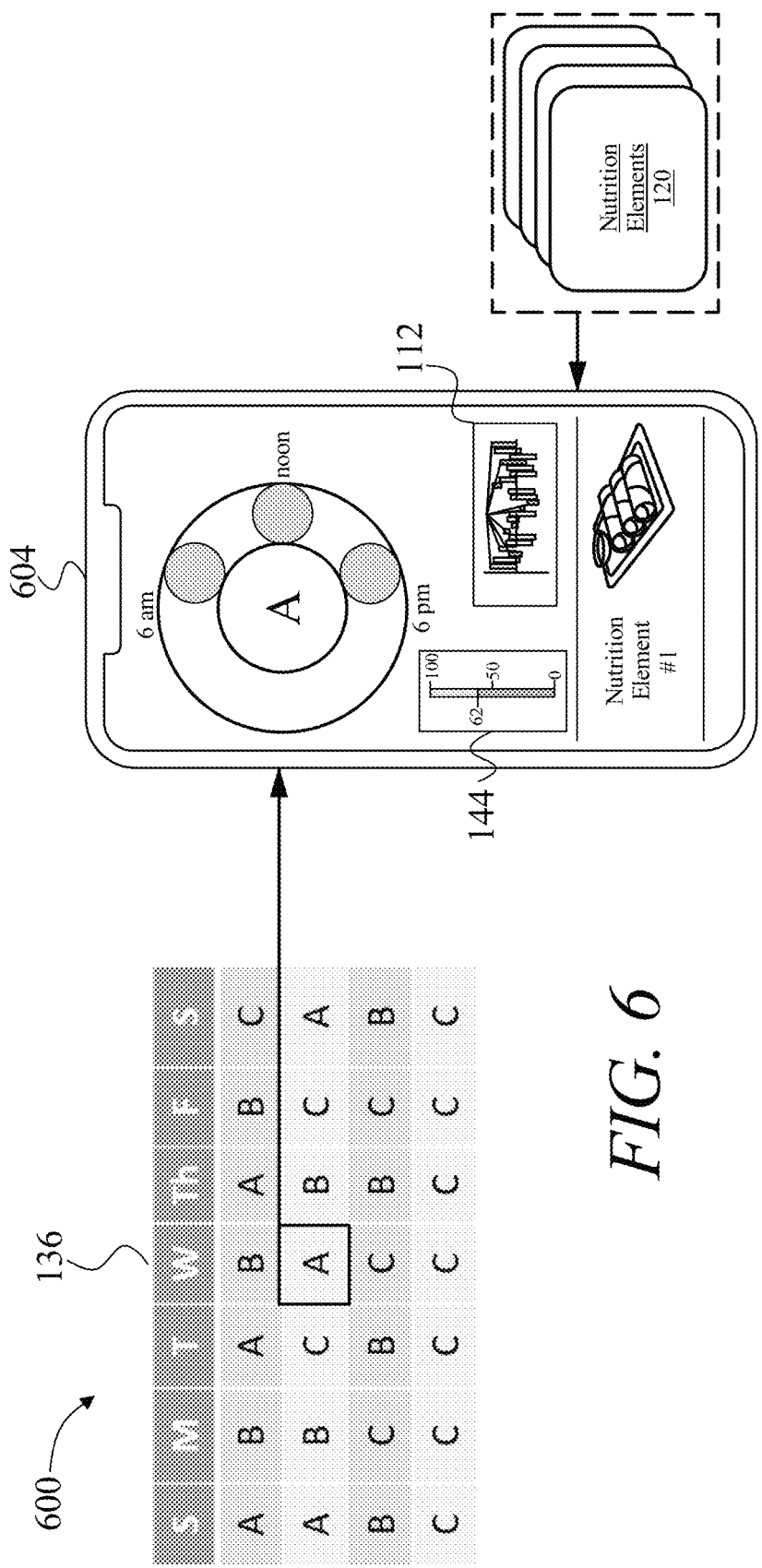
FIG. 6 is a diagrammatic representation of a user device.

Referring now to FIG. 6, a non-limiting exemplary embodiment 600 of a user device 604 is illustrated. User device 604 may include computing device 104, a "smartphone," cellular mobile phone, desktop computer, laptop, tablet computer, internet-of-things (IOT) device, wearable device, among other devices. User device 604 may include any device that is capable for communicating with computing device 104, nourishment plan database 304, or able to receive, transmit, and/or display, via a graphical user interface, cancer profile 112, nutrition element 120, nourishment plan 140, nourishment score 148, among other outputs from system 100. User device 604 may provide a cancer profile 112, for instance as a collection of metrics determined from cancer biomarker 108 data. User device 604 may provide cancer category 124 that was determined as a function of malignancy parameters enumerated in cancer profile 112. User device 604 may provide data concerning nutrient amounts 132, including the levels of specific nutrients, nutrient ranges, nutrients to avoid, etc. User device 604 may link timing of foods to preemptive ordering interface for ordering a nutrition element 120, for instance and without limitation, through a designated mobile application, mapping tool or application, etc., and a radial search method about a user's current location as described in U.S. Nonprovisional application Ser. No. 17/087,745, filed Nov. 3, 2020, titled "A METHOD FOR AND SYSTEM FOR PREDICTING ALIMENTARY ELEMENT ORDERING BASED ON BIOLOGICAL EXTRACTION," the entirety of which is incorporated herein by reference. User device 604 may display nutrient elements 120 as a function of location, for instance and without limitation, as described in User device 604 may link nourishment consumption program 120 to a scheduling application, such as a 'calendar' feature on user device, which may set audio-visual notifications, timers, alarms, and the like. May select locations for nutrition elements 120 based on entity affinity to cancer research, cancer charity, etc.

Figure 7:
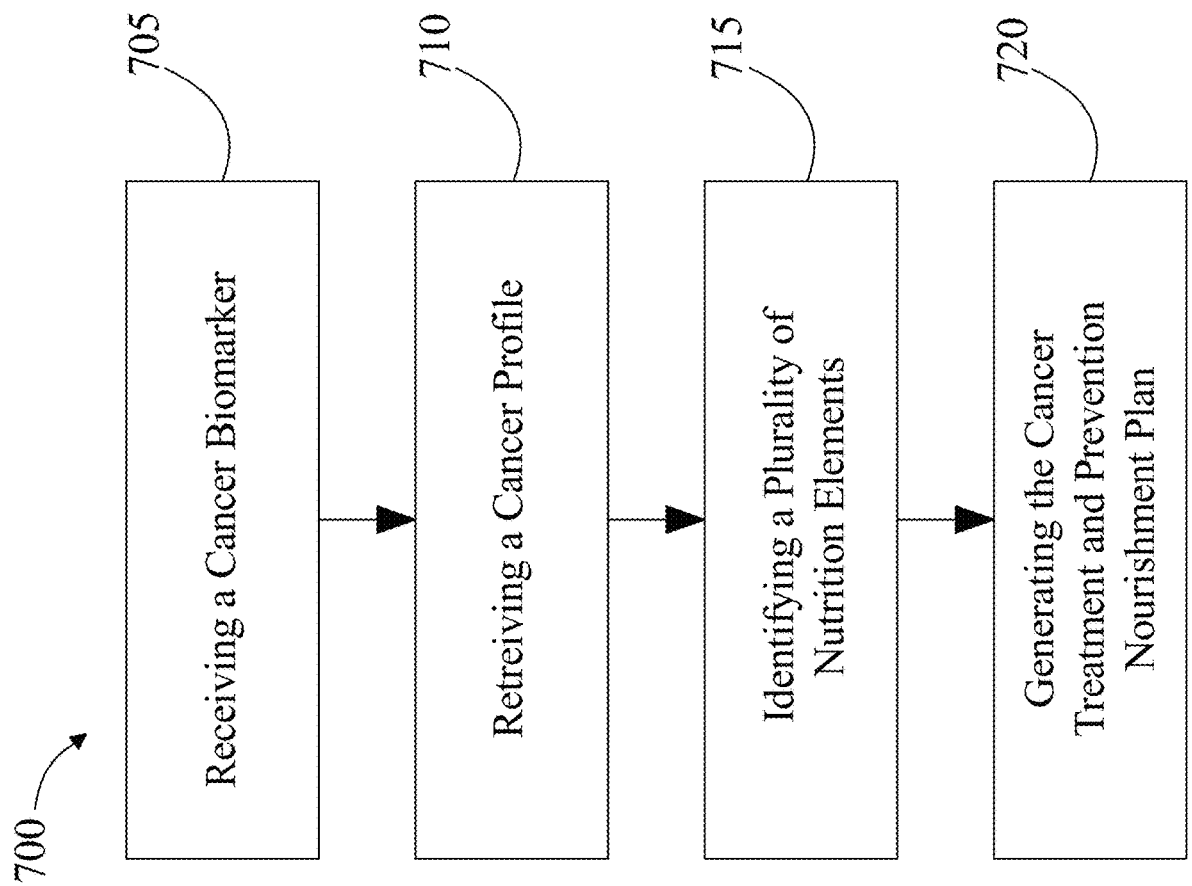
FIG. 7 is a block diagram of a workflow of a method for generating a cancer alleviation nourishment plan.

Referring now to FIG. 7, an exemplary embodiment 700 of a method for generating a cancer alleviation nourishment plan is illustrated. At step 705, the method including a computing device 104 configured for receiving at least a cancer biomarker 108 relating to a user. Receiving at least the cancer biomarker 108 may include receiving a result of one or more tests relating the user; this may be implemented, without limitation, as described above in FIGS. 1-6.

Still referring to FIG. 7, at step 710, method includes retrieving, by a computing device 104, a cancer profile 112 related to the user. of a plurality of malignancy parameters as a function of at least the cancer biomarker 108. Retrieving the cancer profile 112 may include receiving cancer profile 112 training data, training a cancer profile machine-learning model 116 with training data that includes a plurality of data entries wherein each entry correlates cancer biomarkers 108 to a plurality of malignancy parameters, and generating the cancer profile 112 as a function of the cancer profile machine-learning model 116 and at least the cancer biomarker; this may be implemented, without limitation, as described above in FIGS. 1-6.

Continuing in reference to FIG. 7, at step 715, method includes identifying, by the computing device 104 and using the cancer profile 112, a plurality of nutrition elements 120 for the user, wherein identifying includes assigning the cancer profile 112 to a cancer category 124, wherein the cancer category 124 is a determination about a current malignancy state of the user, calculating, according to the cancer category 124, a plurality of nutrient amounts 132, wherein calculating a plurality of nutrient amounts 132 includes determining an effect of the plurality of nutrient amounts 132 on the cancer profile 112, and calculating the plurality of nutrient amounts 132 as a function of the effect, wherein the plurality of nutrient amounts 132 is a plurality of amounts intended to result in cancer prevention. Identifying, as a function of the plurality of nutrient amounts 132, the plurality of nutrition elements 120, wherein the plurality of nutrition elements 132 are intended to prevent cancer as a function of the cancer category 124. Assigning the cancer profile 112 to a cancer category 124 may include classifying the cancer profile 112 to a cancer category 124 using a cancer classification machine-learning process 128 and assigning the cancer category 124 as a function of the cancer classification machine-learning process 128 and the cancer profile 112. Determining the effect of the plurality of nutrient amounts 132 on the cancer profile 112 may include retrieving a plurality of predicted effects of the plurality of nutrient amounts 132 on the cancer profile 112 as a function of at least the cancer biomarker 108. Calculating nutrient amounts 132 may include generating training data using the plurality of predicted effects of the plurality of nutrient amounts 132 identified according to the cancer category 124, training a nutrition machine-learning model 136 according to the training data, wherein training data includes a plurality of data entries that correlates the magnitude of nutrient effect to a plurality of nutrient amounts 132 for each cancer category 124, and calculating nutrient amounts 132 as a function of the nutrition machine learning model 136 and the cancer category 124; this may be implemented, without limitation, as described above in FIGS. 1-6.

Continuing in reference to FIG. 1, at step 720, method includes generating, by the computing device 104, using the plurality of nutrition elements 120, the cancer alleviation nourishment plan 140. Generating the cancer alleviation nourishment plan 140 may include generating a nourishment plan classifier 144 using a nourishment classification machine-learning process to classify the plurality of nutrient amounts to the plurality of nutrition elements and outputting the plurality of nutrition elements 120 as a function of the nourishment plan classifier 144. Generating the cancer alleviation nourishment plan 140 may include generating a nourishment score 148, wherein the nourishment score 148 reflects the level of user participation in the cancer alleviation nourishment plan 140. Generating the cancer alleviation nourishment plan 140 may include calculating a change in incidence of cancer as a function of adhering to nourishment plan 140. Generating the cancer alleviation nourishment plan 140 may include receiving a user preference 152 related to the plurality of nutrition elements 120 and modifying the plurality of nutrition elements 120 as a function of the user preference 152; this may be implemented, without limitation, as described above in FIGS. 1-6.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 8:
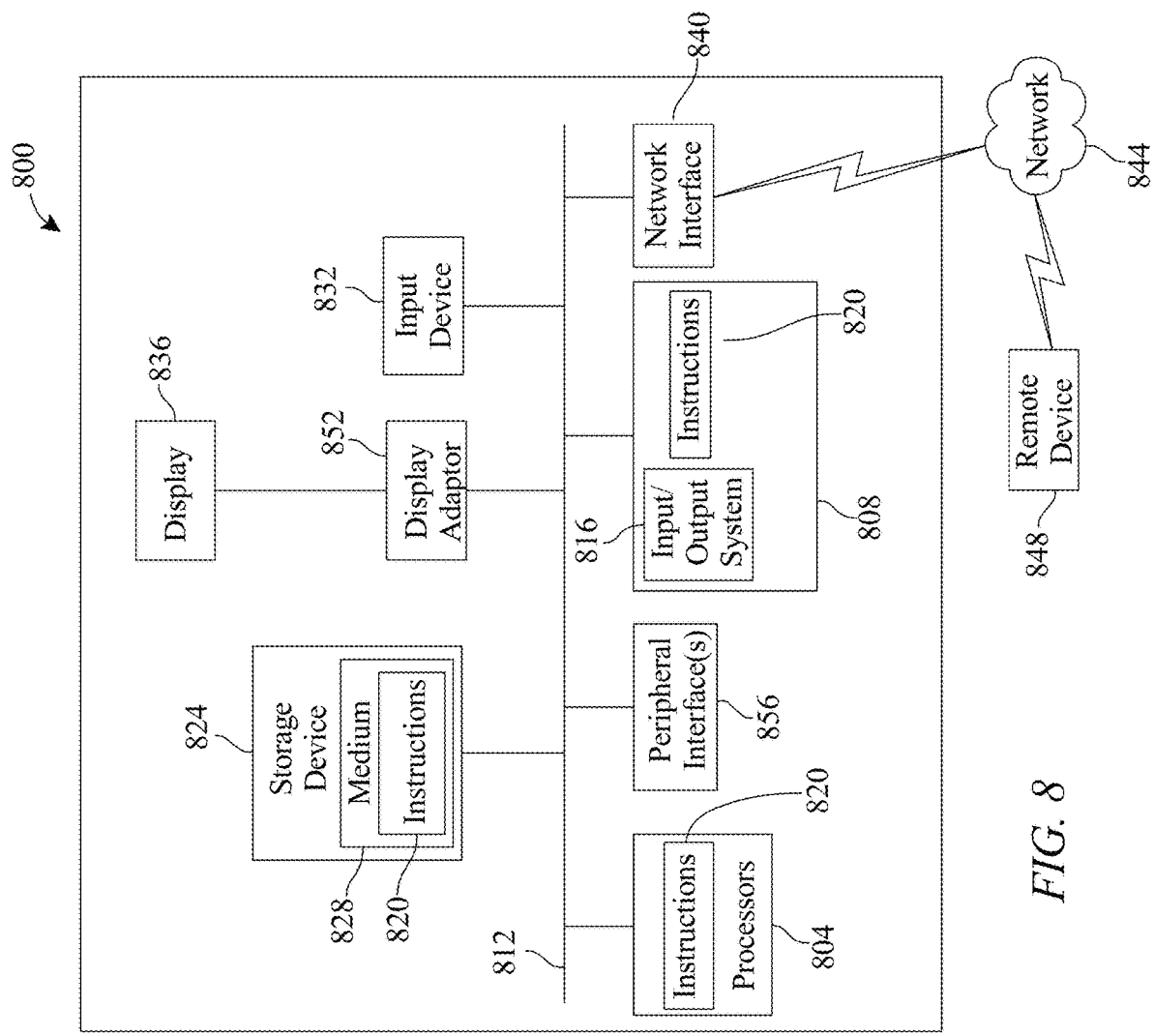
FIG. 8 is a block diagram of a computing system that can be used to implement any one or more of the methodologies disclosed herein and any one or more portions thereof.

FIG. 8 shows a diagrammatic representation of one embodiment of a computing device in the exemplary form of a computer system 800 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 800 includes a processor 804 and a memory 808 that communicate with each other, and with other components, via a bus 812. Bus 812 may include any of several types of bus structures including, but not limited to, a memory bus, a memory controller, a peripheral bus, a local bus, and any combinations thereof, using any of a variety of bus architectures.

Processor 804 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 804 may be organized according to Von Neumann and/or Harvard architecture as a non-limiting example. Processor 804 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC)

Memory 808 may include various components (e.g., machine-readable media) including, but not limited to, a random-access memory component, a read only component, and any combinations thereof. In one example, a basic input/output system 816 (BIOS), including basic routines that help to transfer information between elements within computer system 800, such as during start-up, may be stored in memory 808. Memory 808 may also include (e.g., stored on one or more machine-readable media) instructions (e.g., software) 820 embodying any one or more of the aspects and/or methodologies of the present disclosure. In another example, memory 808 may further include any number of program modules including, but not limited to, an operating system, one or more application programs, other program modules, program data, and any combinations thereof.

Computer system 800 may also include a storage device 824. Examples of a storage device (e.g., storage device 824) include, but are not limited to, a hard disk drive, a magnetic disk drive, an optical disc drive in combination with an optical medium, a solid-state memory device, and any combinations thereof. Storage device 824 may be connected to bus 812 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 824 (or one or more components thereof) may be removably interfaced with computer system 800 (e.g., via an external port connector (not shown)). Particularly, storage device 824 and an associated machine-readable medium 828 may provide nonvolatile and/or volatile storage of machine-readable instructions, data structures, program modules, and/or other data for computer system 800. In one example, software 820 may reside, completely or partially, within machine-readable medium 828. In another example, software 820 may reside, completely or partially, within processor 804.

Computer system 800 may also include an input device 832. In one example, a user of computer system 800 may enter commands and/or other information into computer system 800 via input device 832. Examples of an input device 832 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 832 may be interfaced to bus 812 via any of a variety of interfaces (not shown) including, but not limited to, a serial interface, a parallel interface, a game port, a USB interface, a FIRE-WIRE interface, a direct interface to bus 812, and any combinations thereof. Input device 832 may include a touch screen interface that may be a part of or separate from display 836, discussed further below. Input device 832 may be utilized as a user selection device for selecting one or more graphical representations in a graphical interface as described above.

A user may also input commands and/or other information to computer system 800 via storage device 824 (e.g., a removable disk drive, a flash drive, etc.) and/or network interface device 840. A network interface device, such as network interface device 840, may be utilized for connecting computer system 800 to one or more of a variety of networks, such as network 844, and one or more remote devices 848 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 844, may employ a wired and/or a wireless mode of communication. In general, any network topology may be used. Information (e.g., data, software 820, etc.) may be communicated to and/or from computer system 800 via network interface device 840.

Computer system 800 may further include a video display adapter 852 for communicating a displayable image to a display device, such as display device 836. Examples of a display device include, but are not limited to, a liquid crystal display (LCD), a cathode ray tube (CRT), a plasma display, a light emitting diode (LED) display, and any combinations thereof. Display adapter 852 and display device 836 may be utilized in combination with processor 804 to provide graphical representations of aspects of the present disclosure. In addition to a display device, computer system 800 may include one or more other peripheral output devices including, but not limited to, an audio speaker, a printer, and any combinations thereof. Such peripheral output devices may be connected to bus 812 via a peripheral interface 856. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for generating a nourishment plan for a cancer state, the system comprising:
a computing device, wherein the computing device is configured to:
receive at least a cancer biomarker relating to a user, wherein the cancer biomarker comprises a biological molecule existing within a normal cell;
retrieve a cancer profile related to the user comprising the user's current likelihood of cancer and projected likelihood of cancer;
assign the cancer profile to a cancer category, wherein the cancer category includes a cancer type and a determination of a current malignancy state of the user, wherein the cancer type includes colon cancer, and wherein the current malignancy state of the user comprises a current propensity for developing a malignancy;
identify, using the cancer profile, a plurality of nutrition elements for the user, wherein identifying the plurality of nutrition elements comprises:
calculating, according to the cancer category, a plurality of nutrient amounts, wherein calculating the plurality of nutrient amounts includes:
training a nutrition machine-learning model using training data, wherein the training data includes a plurality of data entries correlating nutrition elements for colon cancer to nutrient amounts; and
calculating the plurality of nutrient amounts as a function of the nutrition machine-learning model and the user's cancer category;
generate, using the plurality of nutrition elements, a nourishment plan for the user's cancer category, the generating of the nourishment plan comprising generating a nourishment score; and display, via a graphical user interface (GUI), a circular graphic comprising circular representations of the plurality of nutrition elements of the nutrition plan, wherein each circular representation comprises a comparative size based on portion sizes of each nutrition element of the nutrition plan, and wherein each circular representation is arranged along the circular graphic corresponding to a time a corresponding nutrition element is expected to be consumed.

2. The system of claim 1, wherein receiving the at least a cancer biomarker further comprises receiving a result of one or more tests relating to the user.

3. The system of claim 1, wherein retrieving the cancer profile further comprises:
receiving cancer profile training data;
training a cancer profile machine-learning model with training data that includes a plurality of data entries wherein each entry correlates cancer biomarkers to a plurality of malignancy parameters; and
generating the cancer profile as a function of the cancer profile machine-learning model and at least the cancer biomarker.

4. The system of claim 1, wherein assigning the cancer profile to the cancer category further comprises:
classifying the cancer profile to the cancer category using a cancer classification machine-learning process; and
assigning the cancer category as a function of the classifying.

5. The system of claim 1, wherein generating the nourishment plan for the user's cancer category further comprises:
generating a nourishment plan classifier using a nourishment classification machine-learning process to classify the plurality of nutrient amounts to the plurality of nutrition elements; and
outputting the plurality of nutrition elements as a function of the nourishment plan classifier.

6. The system of claim 1, wherein generating the nourishment plan for the user's cancer category further comprises calculating a change in incidence of cancer as a function of adherence to the nourishment plan.

7. The system of claim 1, wherein generating the nourishment plan for the user's cancer category further comprises:
receiving a user preference related to the plurality of nutrition elements; and
modifying the plurality of nutrition elements as a function of the user preference.

8. A method for generating a nourishment plan for a cancer state, the method comprising:
receiving, by a computing device, at least a cancer biomarker relating to a user, wherein the cancer biomarker comprises a biological molecule existing within a normal cell;
retrieving, by the computing device, a cancer profile related to the user comprising the user's current likelihood of cancer and projected likelihood of cancer;
assigning, by the computing device, the cancer profile to a cancer category, wherein the cancer category includes a cancer type and a determination of a current malignancy state of the user, wherein the cancer type includes colon cancer, and wherein the current malignancy state of the user comprises a current propensity for developing a malignancy;
identifying, by the computing device, using the cancer profile, a plurality of nutrition elements for the user, wherein identifying the plurality of nutrition elements comprises:
calculating, according to the cancer category, a plurality of nutrient amounts, wherein calculating the plurality of nutrient amounts includes:
training a nutrition machine-learning model using training data, wherein the training data includes a plurality of data entries correlating nutrition elements for colon cancer to nutrient amounts; and
calculating the plurality of nutrient amounts as a function of the nutrition machine-learning model and the user's cancer category;
generating, by the computing device, using the plurality of nutrition elements, a nourishment plan for the user's cancer category, the generating of the nourishment plan comprising generating a nourishment score; and
displaying, via a graphical user interface (GUI), a circular graphic comprising circular representations of the plurality of nutrition elements of the nutrition plan, wherein each circular representation comprises a comparative size based on portion sizes of each nutrition element of the nutrition plan, and wherein each circular representation is arranged along the circular graphic corresponding to a time a corresponding nutrition element is expected to be consumed.

9. The method of claim 8, wherein receiving the at least a cancer biomarker further comprises receiving a result of one or more tests relating to the user.

10. The method of claim 8, wherein retrieving the cancer profile further comprises:
receiving cancer profile training data;
training a cancer profile machine-learning model with training data that includes a plurality of data entries wherein each entry correlates cancer biomarkers to a plurality of malignancy parameters; and
generating the cancer profile as a function of the cancer profile machine-learning model and at least the cancer biomarker.

11. The method of claim 8, wherein assigning the cancer profile to the cancer category further comprises:
classifying the cancer profile to the cancer category using a cancer classification machine-learning process; and
assigning the cancer category as a function of the classifying.

12. The method of claim 8, wherein generating the nourishment plan for the user's cancer category further comprises:
generating a nourishment plan classifier using a nourishment classification machine-learning process to classify the plurality of nutrient amounts to the plurality of nutrition elements; and
outputting the plurality of nutrition elements as a function of the nourishment plan classifier.

13. The method of claim 8, wherein generating the nourishment plan for the user's cancer category further comprises calculating a change in incidence of cancer as a function of adherence to the nourishment plan.

14. The method of claim 8, wherein generating the nourishment plan for the user's cancer category further comprises:
receiving a user preference related to the plurality of nutrition elements; and
modifying the plurality of nutrition elements as a function of the user preference.

15. The system of claim 1, further comprising displaying, via the GUI, the cancer profile.

16. The system of claim 15, wherein the cancer profile is represented as a bar graph.

17. The method of claim 8, further comprising displaying, via the GUI, the cancer profile.

18. The method of claim 17, wherein the cancer profile is represented as a bar graph.

* * * * *